(12) United States Patent
Mousa et al.

(10) Patent No.: US 10,060,934 B2
(45) Date of Patent: Aug. 28, 2018

(54) METHODS FOR SCREENING PATIENTS FOR RESISTANCE TO ANGIOINHIBITION, TREATMENT AND PROPHYLAXIS THEREOF

(71) Applicant: NANOPHARMACEUTICALS LLC, Rensselaer, NY (US)

(72) Inventors: Shaker A. Mousa, Wynantskill, NY (US); Paul J. Davis, West Sand Lake, NY (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 0 days.

(21) Appl. No.: 14/546,440

(22) Filed: Nov. 18, 2014

(65) Prior Publication Data

US 2015/0139934 A1     May 21, 2015

Related U.S. Application Data

(60) Provisional application No. 61/905,325, filed on Nov. 18, 2013.

(51) Int. Cl.
| | | |
|---|---|---|
| *G01N 33/78* | (2006.01) | |
| *G01N 33/74* | (2006.01) | |
| *A61K 47/32* | (2006.01) | |
| *A61K 31/192* | (2006.01) | |
| *A61K 47/10* | (2017.01) | |
| *G01N 33/50* | (2006.01) | |
| *G01N 33/574* | (2006.01) | |

(52) U.S. Cl.
CPC .......... *G01N 33/78* (2013.01); *A61K 31/192* (2013.01); *A61K 47/10* (2013.01); *A61K 47/32* (2013.01); *G01N 33/5088* (2013.01); *G01N 33/574* (2013.01); *G01N 33/743* (2013.01); *G01N 2800/52* (2013.01); *G01N 2800/7014* (2013.01)

(58) Field of Classification Search
None
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |
| 4,650,751 A | 3/1987 | Siegel et al. |
| 4,789,734 A | 12/1988 | Pierschbacher |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Mojocha et al. |
| 5,304,121 A | 4/1994 | Sahatijian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desao et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,677,473 B1 | 1/2004 | Madison et al. |
| 6,740,680 B1 | 5/2004 | Danforth, Jr. et al. |

(Continued)

FOREIGN PATENT DOCUMENTS

| | | |
|---|---|---|
| CA | 2673133 A1 | 11/2008 |
| WO | 9640048 | 12/1996 |

(Continued)

OTHER PUBLICATIONS

Mousa et al. Lung Cancer, 2012, 76, 39-45.*
Davis et al. Circulation Research, 2004, 94, 1500-1506.*
Ditsch et al. Anticancer Research, 2010, 30, 1713-1718.*
Webmd.com (http://www.webmd.com/women/news/20030410/underactive-thyroid-lowers-breast-cancer). Dated Apr. 10, 2003.*
Luethy, A.; et. al. "Autologous stem cell transplantation: Leukapheresis product has anti-angiogenic effects in vivo correlating with neutrophil-derived VEGFR1" Anticancer Research, 2011, v. 31, 9. 3115-3124.*
mythyroid.com. "Blood tests" (http://www.mythyroid.com/bloodtests.html), cached 2005 wayback machine.*

(Continued)

*Primary Examiner* — Mina Haghighatian
*Assistant Examiner* — Erin E Hirt
(74) *Attorney, Agent, or Firm* — Schmeiser, Olsen & Watts, LLP

(57) ABSTRACT

A method for screening a patient for angioinhibition resistance and treating said patient having a disease susceptible to treatment via an anti-angiogenic agent. The screening method includes an assay for identifying the presence of angioinhibition resistance in patients by collecting patient blood or serum and subjecting it to a Chick Chorioallantoic Membrane (CAM) angiogenesis assay configured for accepting a human tumor wherein the human tumor xenograft includes a vasculature system. The screening method and assay further includes steps that include using the CAM results for identifying the endogenous pro-angiogenic non-peptide hormone concentrations of the blood sample by calculating the vascular activity of the vasculature system of the human tumor xenograft in the presence of anti-angiogenic drugs and inducing in the patient, a state of subclinical hypothyroidism prior to commencing anti-angiogenic treatment.

9 Claims, 4 Drawing Sheets

(56) References Cited

U.S. PATENT DOCUMENTS

| | | |
|---|---|---|
| 6,818,620 B2 | 11/2004 | Bhatnagar |
| 6,882,406 B2 | 4/2005 | Kurt et al. |
| 7,638,558 B2 | 12/2009 | Breitenkamp et al. |
| 7,807,621 B2 | 10/2010 | Mazar et al. |
| 8,024,209 B2 | 9/2011 | Gaillard et al. |
| 8,515,451 B2 | 8/2013 | Mousa et al. |
| 8,668,926 B1 | 3/2014 | Mousa et al. |
| 8,802,240 B2 | 8/2014 | Davis et al. |
| 9,180,107 B2 | 11/2015 | Mousa et al. |
| 9,198,887 B2 | 12/2015 | Mousa et al. |
| 9,220,788 B2 | 12/2015 | Davis et al. |
| 9,272,049 B2 | 3/2016 | Alexander-Bridges et al. |
| 9,289,395 B2 | 3/2016 | Davis et al. |
| 9,498,536 B2 | 11/2016 | Mousa et al. |
| 9,579,300 B2 | 2/2017 | Mousa et al. |
| 2001/0013728 A | 1/2001 | Oh et al. |
| 2001/0046521 A1 | 11/2001 | Zasloff et al. |
| 2003/0027940 A1 | 2/2003 | Lang et al. |
| 2003/0104999 A1* | 6/2003 | Iozzo ............... A61K 38/1709 514/13.3 |
| 2005/0124862 A1 | 6/2005 | Mousa et al. |
| 2006/0166303 A1 | 7/2006 | Spanuth |
| 2007/0117841 A1 | 5/2007 | Ozes |
| 2008/0081074 A1 | 4/2008 | Gu et al. |
| 2008/0124280 A1 | 5/2008 | Mousa et al. |
| 2008/0199850 A1 | 8/2008 | Sutter et al. |
| 2010/0159021 A1 | 6/2010 | Davis et al. |
| 2011/0052715 A1 | 3/2011 | Davis et al. |
| 2011/0142941 A1 | 6/2011 | Davis et al. |
| 2012/0315320 A1 | 12/2012 | Davis et al. |

FOREIGN PATENT DOCUMENTS

| | | |
|---|---|---|
| WO | 9959548 A1 | 11/1999 |
| WO | 0203914 A2 | 1/2002 |
| WO | 2004069201 A2 | 8/2004 |
| WO | 2010075332 A1 | 7/2010 |

OTHER PUBLICATIONS

Breier et al., "The role of vascular endothelial growth factor in blood vessel formation", Trends in Cell Biol., 6:454_456 (1996) 3 pages.

Bridoux et al., "Semisynthesis and pharmacological activities of Tetrac analogs: Angiogenesis modulators", Bioorg. Med. Chem. Lett., 19:3259-3263 (2009) 5 pages.

Bridoux et al., "Semisynthesis and pharmacological activities of thyroxine analogs: Development of new angiogenesis modulators", Bioorg. Med. Chem. Lett., 20(11):3394-3398 (2010) 5 pages.

Brockhoff et al., "Differential impact of Cetuximab, Pertuzumab and Trastuzumab on BT474 and SK-BR-3 breast cancer proliferation", Cell Prolif., 40:488-507 (2007) 20 pages.

Brooks et al., "Antintegrin a?β3 blocks human breast cancer growth and angiogenesis in human skin", J. Clin. Invest., 96(4):1815-1822 (1995) 8 pages.

Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.

Burgman et al., "Effect of Inhibitors of Poly(ADP-Ribose)Polymerase on the Radiation Resposne of HeLa S3 Cells", Radiat. Res., 119:380-386 (1989) 7 pages.

Carmeliet et al., "Molecular Basis of Angiogenesis Role of VEGF and VE-Cadherin", Ann. N.Y. Acad. Sci., 902:249-264 (2000) 16 pages.

Chanoine et al., "The role of transthyretin in the transport of thyroid hormone to cerebrospinal fluid and brain", Acta Medica Austriaca, 19(Suppl. 1):25-28 (19920) 5 pages.

Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.

Charo et al., "The Vitronectin Receptor a?β3 Binds Fibronectin and Acts in Concert with a51β1 in Promoting Cellular Attachment and Spreading on Fibronectin", J. Cell Biol., 111(6 Pt. 1): 2795-2800 (1990) 6 pages.

Chase et al., "Principles of Radioisotope Methodology", 2nd Ed., Minneapolis, MN. Burgess Publ. Co., 1962, pp. 68, 87-90. 7 pages.

Chavakis et al., "Kinetics of integrin expression in the mouse model of proliferative retinopathy and success of secondary intervention with cyclic RGD peptides", Diabetologia, 45:262-267 (2002) 6 pages.

Cheng et al., "Molecular Aspects of Thyroid Hormone Actions", Endocri. Rev., 31(2): 139-170 (2010) 32 pages.

Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36):17703-17711 (1987) 9 pages.

Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.

Chiaguri et al., "Anoikis: A necessary death program for anchorage-dependent cells", Biochem. Pharmacol., 76:1352-1364 (2008) 13 pages.

Chinese Office Action for Application No. 2004800331846 dated Mar. 5, 2010 7 pages.

Chinese Office Action for Application No. 2004800331846, dated Nov. 30, 2007, cited CN 1126589. 6 pages.

Clifton et al., "Marked Protection by Moderate Hypothermia After Experimental Traumatic Brain Injury", J. Cereb. Blood Flow Metab., 11(1):114-121 (1991) 9 pages.

Cody et al., "Molecular modeling of the thyroid hormone interactions with a?β3 integrin", Steriods, 72:165-170 (2007) 6 pages.

Cohen-Jonathan et al., "a?β3 integrin pathway controls glioma radioresistance through ILK", Proc. Amer. Assoc. Cancer Res., 47:5180 (2006) (Abstract Only) 2 pages.

Cohen-Jonathan et al., "Radioresistance Induced by the High Molecular Forms of the Basic Fibroblast Growth Factor IS Associated with an increased G2 Delay and a Hyperphosphorylation of p34CDC2 in HeLa Cells", Cancer Res., 57:1364-1370 (1997) 7 pages.

Cox et al., "The repair of potentially lethal damage in X-irradiated cultures of normal and ataxia telangiectasia human fibroblasts", Int. J. Radiat. Biol., 39(4):357-365 (1981) 9 pages.

Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.

D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.

Database BIOSIS [Online] Bioscience Information Service, Philadelphia, PA, US; Nov. 16, 2003, Mousa et al., "Discovery of pro-angiogenic effects of thyroid hormone and analogs", Accession No. PREV200400161659 (Abstract).

Davis et al., "Acting via a Cell Surface Receptor, Thyroid Hormone is a Growth Factor for Glioma cells," Cancer Res., 66(14):7270-7275 (2006) 6 pages.

Davis et al., "Cell-surface receptor for thyroid hormone and tumor cell proliferation", Expert Reviews in Endicrinology and Metabolism, 1(6):753-761 (2006) 10 pages.

Davis et al., "Mechanisms of nongenomic actions of thyroid hormone", Frontiers Neuroendocrinol., 29:211-218 (2008) 8 pages.

Davis et al., "Proangiogenic Action of Thyroid Hormone is Fibroblast Growth Factor-Dependent and is initiated at the Cell Surface." Cir. Res., 94(2004):1500-1506 7 pages.

Davis et al., "Promotion by thyroid hormone of cytoplasm-to-nucleus shutting of thyroid hormone receptors", Steroids, 73:1013-1017 (2008) 5 pages.

Davis et al., "Thyroxine Promotes Association of Mitogen-activated Protein Kinase and Nuclear Thyroid Hormone Receptor (TR) and Causes Serine Phosphorylation of TR", J. Biol. Chem., 275(48):38032-38039 (2000) 8 pages.

(56) References Cited

OTHER PUBLICATIONS

Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane But Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573 (1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Oncocl., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an In Vitro Hollow-Fiber Model System", Antimicrob. Agents Chemother., 46(2):464-470 (2002) 7 pages.
Dupont et al., "Antiangiogenic and antimetastatic properties of Neovastat (?-941), an orally active extract derived from cartilage tissue", Clin. Experim. Metastasis, 19:145-153 (2002) 9 pages.
Edwards et al., "Ttypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10.(1983) 10 pages.
Ely and Berne, "Protective Effects of Adenosine in Myocardial Ischemia", Circulation, 85:893-904 (1992) 13 pages.
Ethier et al., "Adenosine stimulates proliferation of human endothelial cells in culture", Am. J. Physiol., 265:H131-H138.
Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.
Faden et al., "Endogenous Opioid Immunoreactivity in Rat Spinal Cord Following Traumatic Injury", Ann. Neurol., 17 (4):386-390 (1985) 5 pages.
Faden, A.I., "Experimental Neurobiology of Central Nervous System Trauma", Crit. Rev. Neurobiol., 7(3/4):175-186 (1993) 13 pages.
Feeney et al., "Amphetamine, Haloperidol, and Experience Interact to Affect Rate of Recovery After Motor Cortex Injury", Science, 217(4562):855-857 (1982) 4 pages.
Fei et al., "P53 and radiation responses", Oncogene, 22:5774-5783 (2003) 10 pages.
Felding-Habermann et al., "Integrin activation controls metastasis in human breast cancer", Proc. Natl. Acad. Sci. U.S.A., 98(4):1853-1858 (2001) 6 pages.

Feng et al., "Fibrin and Collagen Differentially Regulate Human Dermal Microfascular Endothelial Cell Integrins: Stablization of a?/β3 mRNA by Fibrin", J. Invest. Dermatol., 113(6):913-919 (1999) 7 pages.
Fife et al., "Effects of tetracyclines on angiogenesis in vitro", Cancer Letters, 153:75-78 (2000) 4 pages.
Folkman, J., "Angiogenesis in cancer, vascular, rheumatoid and other disease", Nat. Med., 1(1):27-31 (1995) 5 pages.
Freese et al., "Characterization and mechanism of glutamate neurotoxicity in primary striatal cultures", Brain Res., 521(1/2):254-264 (1990) 12 pages.
Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.
Fujii et al., "Crystal Structure of Trimestatin, a Disintegrin Containing a Cell Adhesion Recognition Motif RGD", J. Mol. Biol., 332:1115-1122 (2003) 8 pages.
Gavrieli et al., "Identification of Programmed Cell Death In Situ via Specific Labeling of Nuclear DNA Fragmentation", J. Cell. Biol., 119(3):493-501 (1992) 9 pages.
GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.
Geng et al., "A Specific Antagonist of the p110s Catalytic Component of Phosphatidylinositol 3'-Kinase, IC486068, Enchances Radiation-Induced Tumor Vascular Destruction", Cancer Res., 64:4893-4899 (2004) 7 pages.
Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.
Gladson, C.L., "Expression of integrin a?β3 in Small Blood Vessels of Giioblastoma Tumors", J. Neurpath. Exp. Neurol., 55(11):1143-1149(1996) 7 pages.
Glinskii et al., "Modification of survival pathway gene expression in human breast cancer cells by tetraiodothyroacetic acid (tetrac)", Cell Cycle, 8(21):3562-3570 (2009) 9 pages.
Glinsky et al., "Classification of Human Breast Cancer Using Gene Expression Profiling as a Component of the Survival Predictor Algorithm", Clin. Cancer Res., 10:2272-2283 (2004) 12 pages.
Glinsky et al., "Gene expression prfiling predicts clinical outcome of prostate cancer", J. Clin. Invest., 113(6):913-923 (2004) 11 pages.
Glinsky et al., "Microarray analysis identifies a death-from-cancer signature predicting therapy failure in patients with multiple types of cancer", J. Clin. Invest., 115(6):1503-1521 (2005) 19 pages.
Glinsky et al., "Microarray Analysis of Xenograft-Derived Cancer Cells Lines Representing Multiple Experimental Models of Human Prostate Cancer", Mol. Carcinog., 37:209-221 (2003) 13 pages.
Goldstein et al., "Influence of Lesion Size and Location on Amphetamine-Facilitated Recovery of Beam-Walking in Rats", Behav. Neurosci., 104(2):320-327 (1990) 9 pages.
Goldstein, A., "Estimating the Error Variance and the Confidence Interval for a Regression Line", in Biostatistics, The MacMillan Co., New York, pp. 139-146 (1964) 10 pages.
Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.
Grant, D.B., "Monitoring TSH concentrations during treatment for gongenital hypothyroidism", Arch. Disease Childhood, 66:669-670 (1991) 2 pages.
Gregoriadis, "Liposomes", in Drug Carriers in Biology and Medicine, Chapter 14, pp. 287-341, Academic Press (1979) 57 pages.
Guigon et al., "Regulation of β-Catenin by a Novel Nongenomic Action of Thyroid Hormone β Receptor", Mol. Cell. Biol., 28(14):4598-4608 (2008) 11 pages.

(56) References Cited

OTHER PUBLICATIONS

Hahn et al., "Plateau-phase cultures of mammalian cells: An in vitro model for human cancer", Curr. Top. Radiat. Res. Q., 8:39-83 (1972) 45 pages.

Halks-Miller et al., "CCR1 Immunoreactivity in Alzheimer's Disease Brains", Society for Neuroscience Meeting, Abstract #787.6, vol. 24 (1998) Abstract Only. 1 page.

Hansebout, R.R., "A Comprehensive Review of Methods of Improving Cord Recovery After Acute Spinla Cord Injury", in Early Management of Acute Spinal Cord Injury, pp. 181-196 (1982) 16 pages.

Hartert, H., "Blutgerinnungsstud Mit Der Thrombelastogeraphie, Einem Neuen Untersuchungsverfahren", Klinische Wochenschrift 26(37/38):577-583 (1948) German Language Only. 9 pages.

Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.

Heller et al., "Inhibition of potentially lethal damage recovery by altered pH, glucose utilization and proliferation in plateau growth phase human glioma cells", Int. J. Radiat. Biol., 66(1):41-47 (1994) 7 pages.

Hercbergs et al., "GL261 brain tumor cells: responses to signle or fractionated x-irradiation with the a?β3 integrin tyroxine receptor antagonist tetrac (tetraiodothyroacetic acid)", 20th EORTC-NCI-AACR Symposium on Molecular Targets and Cancer Therapeutics, Geneva, Switzerland, Oct. 2008.

Hercbergs et al., "GL261 brain tumor cells: responses to single or fractionated x-irradiation with the a?β3 integrin tyroxine receptor antagonist tetrac (tetraiodothyroacetic acid)", Euro. J. Cancer, 6(12):172 (Abstract Only) 4 pages.

Hercbergs et al., "Propylthiouracil-induced Chemical Hypothyroidism with High-Dose Tamoxifen Prolongs Survival in Recurrent High Grade Ciioma: A Phase I/II Study", Anticancer Res., 23:617-626 (2003) 10 pages.

Hercbergs, A., "The Thyroid Gland as an Intrinsic Biologic Response-Modifier in Advanced Neoplasia—A Novel Paradigm", in vivo, 10:245-247 (1996) 3 pages.

Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.

Hercbergs, et al., "Radiosensitization of GL261 glioma cells by tetraiodothyroacetic acid (tetrac)", Cell Cycle, 8(16):2586-2591 (2009) 6 pages.

Hermanson, "Modification with Synthetic Polymers", in Bioconjugate Tech., Ch. 15, Academic Press, San Diego, CA, pp. 617-618 (1996) 4 pages.

Hoff et al., "Medullary Thyroid Carcinoma", Hematol. Oncol. Cin. North Am., 21(3):475-488 (2007) 14 pages.

Horuk et al., "Expression of Chemokine Receptors by Subsets of Neurons in the Central Nervous System", J. Immunol., 158:2882-2890 (1997) 9 pages.

Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.

Hudlicka et al., "Factors involved in capillary growth in the heart", Mol. Cell. Biochem, 147:57-68 (1995) 12 pages.

Igarashi et al., "Techniques Supporting Angiogenesis Therapy 2: DDS Technique Supporting Regenerative Medicine." Inflamm. Immun. 10.6(2002):652-658 7 pages.

Illario et al., "Fibronectin-Induced Proliferation in Thyroid Cells is Mediated by a?β3 Integrin through Ras/Raf-1/b and Calcium/CaMKII Signals", J. Clin. Endocrinol. Metab., 90(5):2865-2873 (2005) 9 pages.

Ingerman-Wojenski et al., "Evaluation of electrical aggregometry: comparison with optial aggregometry, secretion of ATP, and accumulation of radiolabeled platelets", J. Lab. Clin. Med., 101(1):44-52 (1983) 10 pages.

Iwata et al., "A new, convenient method for the preparation of 4-[18F]fluorobenzyl halides", Applied Radiation and Isotopes, 52(1):87-92 (2000) 7 pages.

Jain, K.K., "Strategies and technologies for drug delivery systems", TIPS, 19:155-157 (1998) 5 pages.

Janssen et al., "Pathogenesis of Spinal Cord Injury and Newer Treatments—A Review", Spine, 14(1):23-32 (1989) 11 pages.

Jeffrey et al., "The preparation and characterisation of poly(lactide-co-glycolide) microparticles. 1. Oil-in-water emulsion solvent evaporation", Int. J. Pharm., 77:169-175 (1991) 7 pages.

Jonker et al., "Cetuximab for the Treatment of Colorectal Cancer", N. Engl. J. Med., 357(20):2040-2048 (2007) 9 pages.

Jordan et al., "Thyroid Status is a Key Modulator of Tumor Oxygenation: Implication for Radiation Therapy", Radiat. Res., 168:428-432 (2007) 5 pages.

Kalofonos et al., "Monoclonal Antibodies in the Management of Solid Tumors", Curr. Top. Med. Chem., 6:1687-1705 (2006) 19 pages.

Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.

Kastan et al., "A Mammalian Cell Cycle Checkpoint Pathway Utliziing P53 and GADD45 is Defective in Ataxia-Telangiectasia", Cell. 71:587-597 (1992) 11 pages.

Kawasuji et al., Jap. Circ. J., 63(Suppl. 1):65 (1999) Japanese Abstract Only. 3 pages.

Kerr et al., "Novel Small Molecule a? Integrin Antagonists: Comparative Anti-Cancer Efficacy with Known Angiogenesis Inhibitors", Anticancer Res., 19:959-968 (1999).

Kerr et al., "Small molecule a? integrin antagonists: novel anticancer agents", Exp. Opin. Invest. Drugs, 9 (6):1271-1279 (2000) 9 pages.

Kim et al., "Regulation of Antiogenesis in Vivo, by Ligation of Integrin a5111 with the Central Cell-Binding Domaing of Fibronectin", Am. J. Pathol., 156(4): 1345-1362 (2000) 18 pages.

Kim et al., "Soluble Flt-1 gene delivery using PEI-g-PEG-RGD conjugate for anti-angiogenesis", J. Control Release, 106:224-234 (2005) 11 pages.

Kimelberg, H.K., "Astrocytic Edema in CNS Trauma", J. Neurotrauma, 9(Suppl. 1):S71-S81 (1992) 12 pages.

Kitevska et al., "Caspase-2: controversial killer or checkpoint controller?", Apoptosis, 14:829-848(2009) 20 pages.

Kleczkowska et al., "Differntial poly(ADP-ribose) metabolism in repair-proficient and repair-deficient murine lymphoma cells", Mut. Res., 235:93-99 (1990) 7 pages.

Klunk et al., "Development of Small Molecule Probes for the Beta-Amyloid Protein of Alzheimer's Disease", Neurobiol. Aging, 15(6):691-698 (1994) 8 pages.

Kobayashi et al., "Drug Delivery Catheter." Surg. Front. 9.1(2002):55-57 3 pages.

Konno et al., "Antiogenetic therapy for carcinoma", Igaku No Ayumi, 194(10): 824-828 (2000) 5 pages.

Koutras et al., "Antiproliferative effect of exemestane in lung cancer cells", Mol. Cancer, 8(1):109 (2009) 12 pages.

Koyama et al., "Recent Status and Future Perspectives in Therapeutic Angiogenesis", Prog. Med., 22(12):3070-3076 (2002) (English Abstract) 7 pages.

Kramer et al., "Human Microvascular Endothelial Cells Use β1 and β3 Integrin Receptor Complexes to Attach to Laminin", J. Cell Biol., 111:1233-1343 (1990) 11 pages.

Kumar et al., "Enhancing Effect of Thyroxine on Tumor Growth and Metastases in Syngeneic Mouse Tumor Systems", Cancer Res., 39:3515-3518 (1979) 4 pages.

Kuroki et al., "Diabetic retinopathy—The mechanisms of the ocular neovascularization of the development of anti-angiogenic drugs-", Nippon Rinsho, 57(3):584-589 (1999) (English Abstract Only) 6 pages.

Kwok et al., "Differences in EGF rated radiosensitisation of human squamous carcinoma cells with high and low Number of EGF receptors", Br. J. Cancer, 64:251-254 (1991) 4 pages.

(56) References Cited

OTHER PUBLICATIONS

Lameloise et al., "Differences between the effects of thyroxine and tetraiodothyroacetic acid on TSH suppression and cardiac hypertrophy", Eur. J. Endocrinol., 144:145-154 (2001) 10 pages.

Lawler et al., "Cell Attachment to Thombospondin: The Role of ARG-GLY-ASP, Calcium and Integrn Receptors", J. Cell Biol., 107(6 Pt. 1): 2351-2361 (1988) 11 pages.

Letterio et al., "Maternal Rescue of Transforming Growth Facotr-β1 Null Mice", Science, 264:1936-1938 (1994) 4 pages.

Li et al., "Requirement of hypoxia-inducible factor-1a down-regulation in mediating the antitumor activity of the anit-epidermal growth factor receptor monoclonal antibody cetuximab", Mol. Cancer Ther., 7(5):1207-1217 (2008) 11 pages.

Lin et al., "Androgen-induced human breast cancer cell proliferation is mediated by discrete mechanisms in estrogen receptor-a-positive and -negative breast cancer cells", J. Steroid Biochem. Mol. Biol., 113:182-188 (2009) 7 pages.

Lin et al., "Identification of the Putative MAP Kinase Docking Site in the Thyroid Hormone Receptor-β1 DNA-Binding Domain: Functional Consequences of Mutations at the Docking Site", Biochem., 42:7571-7579 (2003) 9 pages.

Lin et al., "Integrin a?β3 contains a receptor site for resveratrol", FASEB J., 20(10): 1742-1744 (2006) 3 pages.

Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.

Lin et al., "Resveratrol Causes COX-2- and p53-Dependent Apoptosis in Head and Neck Squamos Cell Cancer Cells", J. Cell Biochem., 104:2131-2142 (2008) 12 pages.

Lin et al., "Resveratrol Induced Serine Phosphorylation of p53 Causes Apoptosis in a Mutant p53 Prostate Cancer Cell Line", J. Urol., 168:748-755 (2002) 8 pages.

Lin et al., "Resveratrol is pro-apoptotic and thyroid hormone is anti-apoptotic in glioma cells: both actions are integrin and ERK mediated", Carcinogenesis, 29(1):62-69 (2008) 8 pages.

Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.

Lin et al., "Thyroid hormone is a MAPK-dependent growth factor for thyroid cancer cells and is anti-apoptotic", Steriods, 72:180-187 (2007) 8 pages.

Liu et al., "Calcineurin Is a Common Target of Cyclophilin-Cyclosporin A and FKBP-FK506 Complexes", Cell, 66:807-815 (1991) 9 pages.

Lorger et al., "Activation of tumor cell integrin a?β3 controls angiogenesis and metastatic growth in the brain", Proc. Natl. Acad. Sci. U.S.A., 106(26):10666-10671 (2009) 7 pages.

Louie et al., "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.

Luidens et al., "Thyroid hormone and angiogenesis", Vascular Pharmacology, 52(3-4):142-145 (2010) 4 pages.

Lyons et al., "The Expression of an N-CAM Serum Fragment is Positively Correlated with Severity of Negative Featues in Type II Schizophrenia", Biol. Psychiatry, 23:769-775 (1988) 7 pages.

Ma, et al., "Use of Encapsulated Single Chain Antibodies for Induction of Anti-Idiotypic Humoral and Cellular Immune Responses", J. Pharm. Sci., 87:1375-1378 (1998). 4 pages.

Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.

Mandelin et al., "Extracellular and Intracellular Mechanisms That Mediate the Metastatic Activity of Exogenous Osteopontin", Cancer, 115:1753-1764 (2009) 12 pages.

Mangale et al., "Identification of genes regulated by an interaction between a?β3 integrin and vitronectin in murine decidua", Reprod. Fertil. Dev., 20:311-319 (2008) 10 pages.

Markgraf et al., "Sensorimotor and cognitive consequences of middle cerebral artery occlusion in rates", Brain Res., 575(2):238-246 (1992) 10 pages.

Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.

Masson-Gadais et al., "Integrin a?β3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.

McCarty et al., "Promises and Pitfalls of Anti-Angiogenic Therapy in Clinical Trials." Trends Mol. Med. 9.2(2003):53-58 6 pages.

Meneses et al., "Recombinant angiostatin prevents retinal neovascularization in a murine proliferative retinopathy model", Gene Therapy, 8(8):646-648 (2011) 3 pages.

Mezosi et al., "Nongenomic effect of thyroid hormone on free-radical production in human polymorphonuclear leukocytes", J. Endocrinol., 185:121-129 (2005) 9 pages.

Mishkin et al., "Increased Survival of Rats Bearing Morris Hepatoma 7800 after Induction of Hypothroidism", Cancer Res., 39:2371-2375 (1979) 5 pages.

Miyaguchi et al., "Correlation of Epidermal Growth Factor Receptor and Radiosensitivity in Human Maxillary Carcinoma Cell Lines", ActaOtolaryngol., 118:428-431 (1998) 4 pages.

Moeller et al., "Cytosolic Action of Thyroid Hormone Leads to Induction of Hypoxia-inducible Factor-1a and Glycolytic Genes", Molec. Endo., 19(12):2955-2963 (2005) 9 pages.

Moeller et al., "Thyroid hormone mediated changes in gene expression can be initiated by cytosolic action of the thyroid hormone receptor beta through the phosphatidylinositol 3-kinase pathway", Nuclear Receptor Signaling, 4: E020 (2006) 4 pages.

Mohamed et al., "Wound healing properties of cimetidine in vitro", Drug Intel!. Clin. Pharm., 20(12):973-975 (1986) 4 pages.

Monferran et al., "a?β3 and a?β5 integrins control glioma cell response to ionising radiation through ILK and RhoB", Int. J. Cancer, 123:357-364 (2008) 8 pages.

Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.

Moreno et al., "Metabolic Effects of Thyroid Hormone Derivatives", Thyroid, 18(2):239-253 (2008) 15 pages.

Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18 (2):239-253 (2008) 15 pages.

Mousa et al., "Cellular and Molecular Mechanisms of Nicotine's Pro-Angiogenesis Activity and Its Potential Impact on Cancer", J. Cell. Biochem., 97:1370-1378 (2006) 9 pages.

Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.

Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.

Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.

Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.

Mousa et al., "The Proangiogenic Action of Thyroid Hormone Analogue GC-1 Is Initiated at an Integrin", J. Cardiovasc. Pharmacol., 46(3):356-360 (2005) 6 pages.

(56) References Cited

OTHER PUBLICATIONS

Mousa, et al., "Pro-angiogenesis action of thyroid hormone and analogs in a three-dimensional in vitro microvascular endothelial sprouting model", Int. Angiol., 25(4):407-413 (2006).
Mousa, S.A., "Mechanisms of Angiogenesis: Potential Therapeutic Targets", in Angiogenesis Inhibotors and Stimulators: Potential Therapeutic Implications, Landes Bioscience, Georgetown, Texas, Chapter I, pp. 1-12 (2000) 14 pages.
Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.
Muller et al., "The Double Life of the Ku Protein: Facing the DNA Breaks and the Extracellular Environment", Cell Cycle, 4(30:438-441 (2005) 4 pages.
Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", Faseb J., 19(3):455-457 (2005) 3 pages.
Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.
Nehls et al., "A Novel Micrcarrier-Based in Vitro Assay for Rapid and Reliable Quantification of Three-Domensional Cell Migration and Angiogenesis", Microvasc. Res., 50(3):311-322 (1995) 12 pages.
Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.
Newcomb et al., "Radiation Sensitivity of GL261 Murine Glioma Model and Enhanced Radiation Response by Flavopiridol", Cell Cycle., 5(1):93-99 (2006) 7 pages.
Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.
Nilsson et al., "Evidence for Multiple Thyroxine-binding Sites in Human Prealbumin", J. Biol. Chem., 246(19):6098-6105 (1971) 8 pages.
Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.
Panyam, et al., "Biodegradable nanoparticles for drug and gene delivery to cells and tissues", Advanced Drug Delivery Reviews, 55: 329-347 (2009) 19 pages.
Oak et al., "Antiangiogenic properties of natural polyphenols from red wine and green tea", J. Nutr. Biochem., 16:1-8 (2005) 8 pages.
Office Action (dated Feb. 25, 2014) for U.S. Appl. No. 13/156,047—Filing Date Jun. 8, 2011.
Office Action (dated Apr. 11, 2013) for U.S. Appl. No. 12/816,287—Filing Date Jun. 15, 2010.
Office Action (dated Apr. 12, 2013) for U.S. Appl. No. 12/751,375—Filing Date Mar. 31, 2010.
Office Action (dated Apr. 2, 2013) for U.S. Appl. No. 13/156,047—Filing Date Jun. 8, 2011.
Panter et al. "Pretreatment with NMDA antagonists limits release of excitatory amino acids following traumatic brain injury", Neurosci. Lett., 136(2):165-168 (1992) 4 pages.
Painter et al., "Membrane initiation of DNA synthesis", Nature, 270:543 (1977) 1 page.
Office Action (dated May 8, 2014) for U.S. Appl. No. 12/816,287, filed Jun. 15, 2010.
Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.
Pages et al., "Signaling Angiogenesis via p42/p44 MAP Kinase Cascade", Ann. N.Y. Acad., Sci., 902:187-200 (2000) 14 pages.

Pardridge, W.M., "Receptor-Mediated Peptide Transport through the Blood-Brain Barrier", Endocrine Rev., 7 (3):314-330 (1986) 18 pages.
Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Patel, D.K., "Clinical Use of Anti-Epidermal Growth Factor Receptor Monoclonal Antibodies in Metastatic Colorectal Cancer", Pharacotherapy, 28(11 Pt.2):31S-41S (2008) 12 pages.
Penno et al., "Rapid and quantitative in vitro measurement of cellular chemotaxis and invasion", Meth. Cell Sci., 19:189-195 (1997) 7 pages.
Pirola, et al., "Resveratrol: One Molecule, Many Targets", IUBMB Life, vol. 60, Issue 5, pp. 323-332. 10 pages.
Plow et al., "Ligand Binding to Integrins", J. Biol. Chem., 275(29):21785-21788 (2000) 4 pages.
Powell, J., "The Serial Analysis of Gene Expression", in Meth. Mol. Biol., Chapter 20, 99:297-319 (2000) 23 pages.
Prichard et al., "Concurrent Cetuximab and Bevacizumab Therapy in a Murine Orthotopic Model of Anaplastic Thyroid Carcinoma", Laryngoscope, 117:674-679 (2007) 7 pages.
Pujol et al., "Letter to the editors: Preventioon of thyroid neoplasm recurrence with Triac and levothyroxine", Clin. Endocrinol., 46(1):121-122 (1997) 2 pages.
Raue et al., "Multiple Endocrine Neoplasia Type 2", Horm. Res., 68(Suppl.5): 101-104 (2007) 4 pages.
Rayalam et al., "Resveratrol induces apoptosis and inhibits adipogenesis in 3T3-L1 adipocytes", Phytother. Res., 22:1367-1371 (2008) 5 pages.
Rebbaa et al., "Novel function of the thyroid hormone analog tetraiodothyroacetic acide: a cancer chemosensitizing and anti-cancer agent", Angiogenesis, 11(3):269-276 (2008) 8 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires a?β3", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1-40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10 (6):638-642 (2004) 5 pages.
Scanlan et al., "Selective thyrmimetics: Tissue-selective thyroid hormone analogs", Curr. Opin. Drug Discov. Dev., 4 (5):614-622 (2001) 9 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat medullary thyroid carcinoma", Nat. Clin. Prac. Endocrinol. Metab., 4(10):22-32 (2008) 11 pages.
Schnell et al., "Expression of alpha v beta 3 integrin in patients with high and low grade glioma", Proc. Amer. Assoc. Cancer Res., 47:226 (2006) Abstract Only. 5 pages.

(56) References Cited

OTHER PUBLICATIONS

Schnell et al., "Expression of Integrin a?β3 in Gliomas Correlates with Tumor Grade and Is not Restricted to Tumor Vasculature", Brain Pathol., 18:378-386 (2008) 9 pages.
Schreiber et al., "Hormone delivery systems to the brain-transhyretin", Exp. Clin. Endocrinol Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-a Are Mediated by 3,5'-Cyclic Adenosine 5'-Monophosphate-Dependent Protein Kinase II", Endo., 145(4): 1708-1717 (2004) 10 pages.
Shih et al., "Inhibitory effect of epidermal growth factor on resveratrol-induced apoptosis in prostate cancer cells is mediated by protein kinase C-a", Mol. Cancer Ther., 3:1355-1363 (2004) 9 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "A?β3/a?β5 integrins-FAK-RhoB: A Novel Pathway for Hypoxia Regulation in Glioblastoma", Cancer Res., 69*8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.
Strieth, et al., "Antiangiogenic combination tumor therapy blocking a?-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Sunwoo et al., "Novel Proteasome Inhibitor PS-341 Inhibits Activation of Nuclear Factor-?B, Cell Survival, Tumor Growth, and Angiogenesis in Squamous Cell Carcinoma", Clin. Cancer Res., 7:1419-1428 (2001) 10 pages.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n in Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.
Tanaka et al., J. Soc. Gastroenterological Surgery, 27(2):360 (1996) 3 pages.
Tang et al., "Resveratrol-induced Cyclooxygenase-2 facilitates p53-dependent apoptosis in human breast cancer cells", Mol. Cancer Ther., 5(8):2034-2042 (2006) 9 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.
Thraves et al., "Radiosensitization of Human Fibroblasts by 3-Aminobenzamide: An Inhibitor of Poly(ADP-Ribosylation)", Radiat Res., 104:119-127 (1985) 9 pages.
Tol et al., "Chemotherapy, Bevacizumab, and Cetuximab in Metastatic Colorectal Cancer", N. Engl. J. Med., 360 (6):563-572 (2009) 10 pages.
Tomanek et al., "A Thyroid Hormone Analog Stimulates Angiogenesis in the Post-infarcted Rat Heart", J. Mol. Cell Cardiol., 30(5):923-932 (1998) 10 pages.
Tomanek et al., "Angiogenesis: New Insights and Therapeutic Potential", Anatomical Record (New Anat.), 261:126-135 (2000) 10 pages.
Tomanek et al., "Early Coronary Angiogenesis in Resposne to Thyroxine: Growth Characteristics and Upregulation of Basic Fibroblast Growth Factor", Circ. Res., 82(5):587-593 (1998) 8 pages.
Tomanek et al., "Growth of the Coronary Vasculature in Hypertrophy: Mechanisms and Model Dependence", Cell. Mol. Bio. Res., 40(2):129-136 (1994) 8 pages.
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.
Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel a? integrin antagonist SM256 and cis-platinum on growth of murine squamos cell carcinoma PAM LY8", Int. J. Oncol., 16(6):1189-1195 (2000) 8 pages.
VanCutsem et al., "Cetuximab and Chemotherapy as Initial Treatment for Metastatic Colorectal Cancer", N. Engl. J. Med., 360:1408-1417 (2009) 10 pages.
Varnes et al., "The Effect of pH on Potentially Lethal Damage Recovery in A549 Cells", Radiat. Res., 108:80-90 (1986) 11 pages.
Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.
Wang et al., "Integrin-associated Protein Stimulates a2β1-dependent Chemotaxis via Gi-mediated inhibition of Adenylate Cyclase and Extracelular-regulated Kinases", J. Cell. Biol., 147:389-399 (1999) 11 pages.
Wen et al., "Prognostic Value of EGFR and TGF-a in Early Laryngeal Cancer Treated With Radiotherapy", Laryngoscope, 106(7):884-888 (1996) 6 pages.
Werdelin et al., "Neuropeptides and neural cell adhesion molecule (NCAM) in CSF from patients with ALS", Acta Neurol. Scand., 79(3):177-181 (1989).
Wilkinson, J.H., "Synthesis of some Possible Metabolites of Thyroxine and Triiodothyronine", Biochem. J., 63:601-605 (1956) 5 pages.
Xia et al., "Chemokines/chemokine receptors in the central nervous system and Alzheimer's disease", J. NeuroVirol., 5:32-41 (1999) 11 pages.
Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.

(56) References Cited

OTHER PUBLICATIONS

Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.
Yanase et al., "Role of N-methyl-D-aspartate receptor in acute spinal cord injury", J. Neurosurg., 83:884-888 (1995) 6 pages.
Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.
Yang, et al., "Enhanced inhibition of adipogenesis and induction of apoptosis in 3T3-L1 adipocytes with combinations of resveratrol and quercetin", Life Sci., 82:1032-1039 (2008) 8 pages.
Yonkers et al., "Sensory Neuron Sodium Current Requires Nongenomic Actions of Thyroid Hormone During Development", J. Neurophysiol., 100:2719-2725 (2008) 7 pages.
Young, W., "Role of Calcium in Central Nervous System Injuries", J. Neurotrauma, 9(Suppl. 1): S9-S25 (1992) 18 pages.
Young, W., "Secondary injury mechanisms in acute spinal cord injury", J. Emerg. Med., 11:13-22 (1993) 11 pages.
Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.
Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.
Zhang et al., "Oestrogen inhibits resveratrol-induced post-translational modification of p53 and apoptosis in breast cancer cells", Br. J. Cancer, 91:178-185 (2004) 8 pages.
Zhang et al., "Quantitative PET Imaging of Tumor Integrin a?β3 Expression with 18F-FRGD2", J. Nucl. Med., 47:113-121 (2006) 9 pages.
Zhen et al., "Synthesis and Amyloid Binding Properties of Rhenium Compleses: Preliminary Progress Toward a Reagent for SPECT Imaging of Alzheimer's Disease Brain", J. Med. Chem., 42:2805-2815 (1999) 11 pages.
Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
Application No. PCT/US2014/66154, International Search Report and Written Opinion, dated Jan. 27, 2015. 23 pages.
Application No. PCT/US2010/038700, Supplemental European Search Report dated Apr. 20, 2015. 7 pages.
Bergers et al., "Modes of resistance to anti-angiogenic therapy", Nat. Rev. Cancer, 8(8):592-603 (2008) 23 pages.
NCI Cancer Drug Information, Cetuximab, 2006,http://www.cancer.gov/cancertopics/druginfo/cetuxinnab,downloaded Jul. 18, 2014.
Gu et al. 2007, Nanotoday 2:14-21.
J Wood, K Bonjean, S Ruetz, A Bellahcene, L Devy, JM Foidart, V Castronovo, JR Green. "Novel Antiangiogenic Effects of the u Bisphosphonate Compound Zoledronic Acid." The Journal of Pharmacology and Experimental Therapeutics, vol. 302, No. 3, 2002, pp. 1055-1061.
M Yalcin, DJ Bharali, L Lansing, E Dyskin, SS Mousa, A Hercbergs, FB Davis, PJ Davis, SA Mousa. "Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.
Office Action (dated Jun. 21, 2011) for U.S. Appl. No. 12/947,389, filed Nov. 16, 2010.
Office Action (dated Apr. 4, 2012) for U.S. Appl. No. 12/947,389, filed Nov. 16, 2010.
Office Action (dated Oct. 17, 2012) for U.S. Appl. No. 12/947,389, filed Nov. 16, 2010.
Office Action (dated Mar. 12, 2014) for U.S. Appl. No. 12/947,389, filed Nov. 16, 2010.
Office Action (dated Apr. 4, 2014) for U.S. Appl. No. 12/947,389, filed Nov. 16, 2010.
Office Action (dated Sep. 4, 2014) for U.S. Appl. No. 12/947,389, filed Nov. 16, 2010.
Office Action (dated May 23, 2012) for U.S. Appl. No. 12/816,287, filed Jun. 15, 2010.
Office Action (dated Oct. 24, 2013) for U.S. Appl. No. 12/816,287, filed Jun. 15, 2010.
Notice of Allowance (dated May 12, 2015) for U.S. Appl. No. 12/816,287.
Office Action (dated Apr. 8, 2013) for U.S. Appl. No. 11/786,723, filed Apr. 11, 2007.
Office Action (dated May 12, 2015) for U.S. Appl. No. 14/078,713, filed Nov. 13, 2013.
Office Action (dated Mar. 24, 2015) for U.S. Appl. No. 13/975,725, filed Aug. 26, 2013.
Office Action (dated Oct. 5, 2012) for U.S. Appl. No. 12/644,493, filed Dec. 22, 2009.
Office Action (dated Oct. 16, 2014) for U.S. Appl. No. 12/644,493, filed Dec. 22, 2009.
Office Action (dated Apr. 16, 2015) for U.S. Appl. No. 13/156,047, filed Jun. 8, 2011.
Office Action (dated Jul. 13, 2012) for U.S. Appl. No. 12/751,375, filed Mar. 31, 2010.
Office Action (dated Jan. 12, 2015) for U.S. Appl. No. 12/751,375, filed Mar. 31, 2010.
Office Action (dated Jun. 3, 2015) for U.S. Appl. No. 12/751,375, filed Mar. 31, 2010.
Office Action (dated Oct. 14, 2014) for U.S. Appl. No. 14/242,041, filed Apr. 1, 2014.
Notice of Allowance (dated Aug. 3, 2015) for U.S. Appl. No. 14/078,713, filed Nov. 13, 2013.
Notice of Allowance (dated Jul. 7, 2015) for U.S. Appl. No. 12/751,375, filed Mar. 31, 2010.
European Office Action for EP Application No. 07867073.4, dated Jul. 16, 2015.
Notice of Allowance (dated Nov. 16, 2015) for U.S. Appl. No. 12/947,389, filed Nov. 16, 2010.
Restriction Requirement (dated Dec. 2, 2015) for U.S. Appl. No. 14/184,889, filed Feb. 20, 2014.
Restriction Requirement (dated Dec. 2, 2015) for U.S. Appl. No. 14/185,010, filed Feb. 20, 2014.
Final Office Action (dated Oct. 9, 2015) for U.S. Appl. No. 13/975,725, filed Aug. 26, 2013.
Advisory Action (dated Dec. 31, 2015) for U.S. Appl. No. 13/975,725, filed Aug. 26, 2013.
Notice of Allowance (dated Nov. 2, 2015) for U.S. Appl. No. 13/256,047, filed Jun. 8, 2011.
Final Office Action (dated Oct. 16, 2015) for U.S. Appl. No. 14/242,041, filed Apr. 1, 2014.
Bergh et al., "Integrin a?β3 contains a cell surface receptor site for thyroid hormone that is linked to activation of mitogen-activated protein kinase and induction of angiogenesis", Endocrinology, 146(7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.

(56) References Cited

OTHER PUBLICATIONS

Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.

Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.

Blight, A.R., "Macrophages and Inflammatory Damage in Spinal Cord Injury", J. Neurotrauma, 9(Suppl. 1):S83-S91 (1992) 10 pages.

Blood et al., "Tumor interactions with the vasculature: angiogenesis and tumor metastasis", Bioch. Biophys. Acta, 1032:89-118 (1990) 30 pages.

Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.

Bornebroek et al., "Potential for imaging cerebral amyloid deposits using 123I-labelled serum amyloid P component and SPET", Cucl. Med. Commun., 17:929-933 (1996) 6 pages.

Bozarth et al., "An improved method for the quantitation of cellular migration: Rose of a?β3 integrin in endothelial and smooth muscle cell migration", Meth. Cell Sci., 19(3):179-187 (1997) 9 pages.

Brachmann et al., "The SIR2 gene family, conserved from bacteria to humans, functions in silencing, cell cycle progression, and chromosome stability", Genes Dev. 9:2888-2902 (1995) 15 pages.

Braughler et al., "Involvement of Lipid Peroxidation in CNS Injury", J. Neurotrauma, 9(Suppl. 1):S1-S7 (1992) 8 pages.

Advisory Action (dated Jan. 21, 2016) for U.S. Appl. No. 14/242,041, filed Apr. 1, 2014.

Restriction Requirement (dated May 5, 2016) for U.S. Appl. No. 14/977,776.

Office Action (dated Sep. 9, 2016) for U.S. Appl. No. 14/185,010, filed Feb. 20, 2014.

Office Action (dated Jun. 17, 2016) for U.S. Appl. No. 13/975,725, filed Aug. 26, 2013.

Notice of Allowance (dated Jul. 19, 2016) for U.S. Appl. No. 14/242,041, filed Apr. 1, 2014.

Restriction Requirement (dated Dec. 3, 2015) for U.S. Appl. No. 14/184,889, filed Feb. 20, 2014.

Office Action (dated May 6, 2016) for U.S. Appl. No. 14/184,889, filed Feb. 20, 2014.

Office Action (dated Oct. 12, 2016) for U.S. Appl. No. 12/644,493, filed Dec. 22, 2009.

Park, T.G., "Bioconjugation of Biodegradable Poly (lactic'glycolic acid) to Protein, Peptide, and Anti-Cancer Drug: An Alternative Pathway for Achieving Controlled Release from Micro- and Nanoparticles." in Polymeric Drugs and Drug Delivery Systems, Ottenbrite R.M. and Kim S.W., eds., Ch. 7, pp. 101-114 (2001).

Oh, Jong Eun, et al., "Conjugation of drug to poly (D,L-lacitic-co-glycoli acid) for controlled release from biodegradable microspheres." Journal of Controlled Release 57, 269-280 (1999).

Leuthy,A.; et al. "Autologous stem cell transplantation: leukapheresis product has anti-angiogenic effects in vivo correlating with neutrophil-derived 'VEGFR1" Anticancer Research, 2001, v.31, 9.3115-3124.

Mythyroid.com. "Blood tests" (Http://222.mythyroid.com/bloodtests.html) cached 2005 wayback machine.

Huang Kuo-Shiang et al. "Combination of baculovirus-mediated gene delivery and packed-bed reactor for scalable production of adeno-associated virus", Human Gene Therapy, Mary Ann Liebert, Inc., publishers, us., vol. 18, No. 11. 2007, pp. 1161-1170.

Hung-Yun Lin et al. "Pharmacodynamic modeling of anti-cancer activity of tetraiodotheyroacetic acid in a perfused cell culture system" Plos Computational Biology, vol. 7, n.2, 2011, p. e1001073.

Office Action (dated Nov. 4, 2016) for U.S. Appl. No. 14/977,776.

Final Office Action (dated Apr. 3, 2017) for U.S. Appl. No. 13/975,725, filed Aug. 26, 2013.

Notice of Allowance (dated Jan. 31, 2018 U.S. Appl. No. 13/975,725, filed Aug. 26, 2013.

Office Action (dated Apr. 24, 2017) for U.S. Appl. No. 12/644,493, filed Dec. 22, 2009.

Restriction Requirement (dated Feb. 9, 2017) for U.S. Appl. No. 15/056,522, filed Feb. 29, 2016.

\* cited by examiner

METHODS FOR SCREENING PATIENTS FOR RESISTANCE TO ANGIOINHIBITION, TREATMENT AND PROPHYLAXIS THEREOF

CROSS REFERENCE TO RELATED APPLICATIONS

This application claims the priority and benefit of U.S. Provisional Application No. 61/905,325, filed Nov. 18, 2013, entitled "THYROID HORMONES, ANALOGS THEREOF, MECHANISMS OF ACTION AND METHODS OF USE", the content of which is incorporated herein by reference.

FIELD OF THE DISCLOSURE

The following relates to methods for screening patients exhibiting resistance to angioinhibition, treatment and prophylaxis thereof and more specifically, to embodiments of assays directed toward identifying elevated endogenous pro-angiogenic non-peptide hormones and endogenous growth factors as well as their contribution to suboptimal efficacy of angioinhibition therapy, and the methods for reducing said suboptimal efficacy.

BACKGROUND

Thyroid hormones, such as thyroxine ($T_4$). L-thyroxine ($LT_4$) and 3,5,3'-triiodo-L-thyronine ($T_3$), and their analogs such as GC-1, DITPA, tetrac and triac, regulate many different physiological processes in different tissues in vertebrates. It was previously known that many of the actions of thyroid hormones are mediated by the thyroid hormone receptor ("TR"). A novel cell surface, integrin $\alpha v \beta 3$ receptor for endogenous thyroid hormone (L-thyroxine, $T_4$, $T_3$) has been identified. The $\alpha v \beta 3$ receptor however, is not a homologue of the nuclear thyroid hormone receptor (TR), but rather, a cell surface receptor that is capable of performing a number of nucleus-mediated events, including pro-angiogenic action of thyroid hormone.

Tetraiodothyroacetic acid (tetrac) is a deaminated analog of $T_4$ that has no agonist activity at the integrin. Instead, tetrac inhibits binding of $T_4$ and $T_3$ to the integrin and the pro-angiogenic action of thyroid hormone analogs at $\alpha v \beta 3$. Inhibition of the angiogenic action of thyroid hormone has been shown in the chick chorioallantoic membrane (CAM) model, in the vessel sprouting model involving human dermal microvascular endothelial cells (HDMEC), and in vivo in the mouse matrigel angiogenesis model.

In the absence of thyroid hormone, tetrac blocks the angiogenic activity of basic fibroblast growth factor (bFGF, FGF2), vascular endothelial growth factor (VEGF) and other pro-angiogenic factors.

Circulating levels of thyroid hormone are relatively stable. Thyroid hormone may increase activity of small molecules that support neovascularization (bradykinin, angiotensin II) and stimulate endothelial cell motility. Therapeutic angio-inhibition in the setting of cancer may be opposed by endogenous thyroid hormone, particularly when a single vascular growth factor is the treatment target. This may be a particular issue in management of aggressive or recurrent tumors. Membrane-initiated actions of thyroid hormone on neovascularization, cell proliferation, membrane ion channels or gene expression effects of the hormone, mediated by thyroid receptors, may be assumed to contribute to "basal activity" or set-points of life processes in intact organisms. The possible clinical utility of cellular events that are mediated by the membrane receptor for thyroid hormone may reside in inhibition of such effect(s) in the contexts of neovascularization or tumor cell growth. Indeed, it has been shown that blocking the membrane receptor for iodothyronines with tetraiodothyroacetic acid (tetrac), a hormone-binding inhibitory analog that has no agonist activity at the receptor, can arrest growth of glioma cells and of human breast cancer cells in vitro.

Despite the promising results of anti-angiogenic pharmaceuticals, angioinhibition as a treatment option for various cancers and debilitating diseases has been met with varying degrees of success. Elevated levels of endogenous circulating pro-angiogenic thyroid hormone in patients receiving anti-angiogenic therapy can lead to resistance in the host patient. This development in resistance may lead to previously successful treatments becoming ultimately ineffective. Therefore, there is a need for an assay to identify and screen for patients who have developed or are at risk of developing a resistance to the anti-angiogenic treatments. Moreover, there is also a need for a treatment and prophylactic method to prevent the formation of the anti-angiogenic resistance in patients.

BRIEF SUMMARY

A first aspect of this disclosure relates to a method for screening a patient for angioinhibition resistance and treating said patient having a disease susceptible to treatment via an anti-angiogenic agent, comprising the steps of collecting a blood or serum sample from the patient, performing a Chick Chorioallantoic Membrane (CAM) angiogenesis assay configured for using the collected blood or serum sample from the patient, wherein the CAM includes a human tumor xenograft having a vasculature system, identifying a concentration of an endogenous pro-angiogenic non-peptide hormone of the blood sample by statistically analyzing a number of vessel branches formed in the presence of the anti-angiogenic agent during the CAM and inducing in the patient, a state of subclinical hypothyroidism.

A second aspect of this disclosure relates to method for prophylactically treating a patient with a disease susceptible to developing resistance to angioinhibition, comprising the steps of inducing subclinical hypothyroidism in the patient, wherein the patient has a normal range of free T4 present and administering to the patient an anti-angiogenic agent that binds to integrin $\alpha v \beta 3$, a chemotherapeutic agent, an anti-inflammatory agent or a combination of agents thereof.

The foregoing and other features of construction and operation will be more readily understood and fully appreciated from the following detailed disclosure, taken in conjunction with accompanying drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus, method, and system are presented herein by way of exemplification and not limitation with reference to the Figures. Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure.

As a preface to the detailed description, it should be noted that, as used in this specification and the appended claims, the singular forms "a", "an" and "the" include plural referents, unless the context clearly dictates otherwise.

Figure 1:
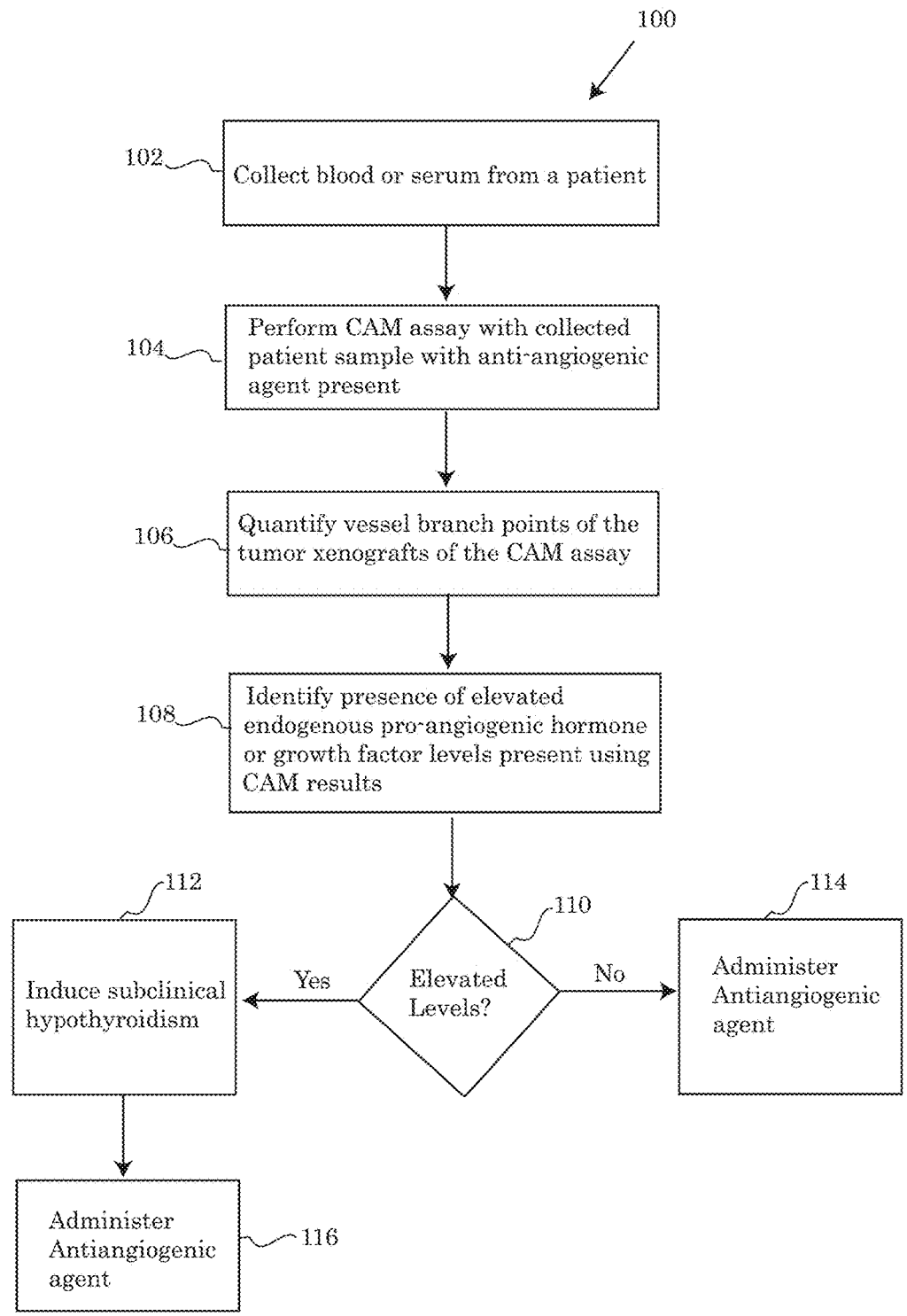
FIG. 1 depicts a schematic view of an embodiment of an assay for screening a patient for host resistance to a disease susceptible to treatment via an anti-angiogenic agent.

Referring to the drawings, FIG. 1 provides a schematic for an embodiment of an assay 100 for screening and identifying patients who may be susceptible to developing or have developed a resistance to angioinhibition. The assay 100 described herein, may assist healthcare professionals by independently identifying each patient's risk of developing resistance to angioinhibition on a case by case basis. Embodiments of the assay 100 may be directed toward identifying and quantifying the amounts of circulating, endogenous, non-peptide hormones that may have a pro-angiogenic function. Endogenous, non-peptide hormones with pro-angiogenic function that may impact the development of resistance to angioinhibition may include thyroid hormone including thyroxine ($T_4$), free thyroxine ($FT_4$) levothyroxine (L-$T_4$) triiodothyronine ($T_3$), as well as other non-peptide hormones such as estrogen, and progesterone.

As the concentration levels of these endogenous, non-peptide hormones increases to elevated levels, the non-peptide hormones may develop resistance to the anti-angiogenic effects of anti-angiogenic agents that may be administered to treat a myriad of diseases. Even at elevated levels within normal ranges, non-peptide hormones such as thyroid hormones may oppose the action of anti-angiogenic agents. However, when the healthcare professionals continue to pursue treatment of diseases after the development of resistance, the anti-angiogenic pathways may be rendered ineffective by the elevated endogenous non-peptide hormones. For example, diseases that may be treated using anti-angiogenic pathways may include, but are not limited to primary or metastatic tumors, adenoid carcinoma, breast cancer, kidney cancer, colon cancer, glioblastoma multiforme, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, carcinoma, stomach cancer, thyroid cancer, diabetic retinopathy, wet macular degeneration, arthritis, Parkinson's Disease, Alzheimer's Disease or a combination of diseases thereof.

Resistance to the angioinhibition properties of anti-angiogenic agents may develop when a patient's endogenous angiogenic non-peptide hormones in their body become elevated close to beyond the upper limit of normal circulating hormone levels. In the exemplary embodiment, of assay 100, the concentration of free thyroxine ($FT_4$) may be the prototypical hormone measured in the collected blood or serum sample from the patient. The assay 100 however, may be also directed at identifying and quantifying the levels of any of the endogenous non-peptide angiogenic hormones previously described. This may include identifying the endogenous pro-angiogenic non-peptide hormone content of the blood or serum sample by calculating the vascular activity of the vasculature system of the human tumor xenograft in the presence of the anti-angiogenic drug.

In addition, the assay 100 may further be used to identify and quantify the presence of one or more associated growth factors that may proliferate to elevated levels in the presence of elevated endogenous pro-angiogenic non-peptide hormones. Initiation and maintenance of a patient's vascular supply which may occur during angiogenesis, may involve local release of vascular growth factors. Thus, as the pro-angiogenic hormones increase, the amount of the resulting growth factors may also increase, providing another measurable endogenous substance to quantify in addition to the pro-angiogenic hormones. Examples of endogenous growth factors that may be measured may include vascular endothelial growth factor (VEGF), basic fibroblast growth factor (bFGF; FGF2), platelet-derived growth factor (PDGF) as well as the discrete receptors for each of these proteins on the cell surface that transduce specific growth factor signals into intracellular and extracellular angiogenesis-related events. Additional growth factors that may also be present and quantified may further include epidermal growth factor (EGF) and insulin-like growth factor-1 (IGF-1).

The first step in the assay 100 may include the step of collecting 102 a blood or serum sample from the patient being screened. The collection process can occur using any known clinical means for safely and effectively withdrawing the sample from the patient's body. The blood or serum sample may provide evidence of total concentrations of endogenous non-peptide hormone circulating within the patient's body. This may allow for doctors and clinicians, to tailor individualized and custom medical care based on the individual levels of pro-angiogenic hormones and/or growth factors identified. Individual care customized for the patient is advantageous over a one size fits all treatment approach because the results of the assay 100 may affect the subsequent treatment steps based on specific individualized results, rather than guessing how a patient may respond based on pools of clinical data from other patients.

After the collecting step 102, wherein the sample is withdrawn, the sample may subsequently be analyzed to identify the patient's levels of endogenous pro-angiogenic non-peptide hormone present. In some embodiments, the CAM assay being performed may be configured for accepting human tumor xenografts wherein the xenografts include a vasculature system. Moreover, the CAM may be performed using the blood or serum sample from the patient being tested. In some embodiments of the assay 100, the analysis and quantification of the blood sample's pro-angiogenic hormone levels may be calculated by performing a Chick Chorioallantoic Membrane (CAM) angiogenesis assay in the presence of one or more anti-angiogenic agents. The inclusion of the anti-angiogenic agent with the CAM, when used in conjunction with the patient's sample may further assist the clinician or doctor in identifying the presence of angioinhibition resistance. For instance, when performing a CAM assay using a patient sample from a patient who has not developed resistance to angioinhibition, a person skilled in the art might expect to observe limited or significantly less vessel branches being formed due to the angioinhibition effect of the anti-angiogenic agent. Conversely, when a patient has developed resistance to angioinhibition, an increasing number of vessel branches will form in lieu of the anti-angiogenic agent's presence.

In the Exemplary embodiment, the CAM being performed using the patient's blood or serum sample may also be performed in the presence of tetrac, triac, or conjugated formulations of tetrac and triac described below in combination with a second anti-angiogenic agent. The tetrac/triac or conjugated form acting at the surface integrin receptor αvβ3, may assist the clinician or doctor in determining whether or not the endogenous hormones in the patient's blood or serum are responsible for blockading and thus preventing the second anti-angiogenic agent from working effectively. For example, if the CAM performed in the presence of an anti-angiogenic agent, such as bevacizumab (trade name Avastin®) and it can be seen that there is an increased amount of new vessel branch points in comparison with a CAM performed in the presence of tetrac/triac or conjugated forms thereof and Bevacizumab, it may be concluded that resistance to bevacizumab has developed due to elevated pro-angiogenic blocking bevacizumab from effectively inhibiting angiogenesis.

Examples of an anti-angiogenic agent that may be used for the CAM assay may include any drug having anti-angiogenic properties. In some embodiments, the anti-angiogenic agent may be an anti-angiogenic thyroid hormone analog and may be referred to as a thyroid hormone antagonist. The thyroid hormone anatagonists may operate by binding to the cell surface receptor αvβ3. The terms "anti-angiogenesis" agent or "anti-angiogenic" agent may also refer to any compound or substance that inhibits or antagonizes angiogenesis, whether alone or in combination with another substance. Examples of anti-angiogenic agents may include tetraiodothyroacetic acid (tetrac), triiodothyroacetic acid (triac), monoclonal antibodies XT 199 or mAb LM609, bevacizumab, itraconazole, carboxyamidotriazole, TNP-470, CM101, IFN-α, IL-12, platelet factor-4, suramin, SU5416, thrombospondin, VEGFR antagonists, angiostatic steroids in combination with heparin, cartilage derived angiogenesis inhibitory factor, matrix metalloproteinase inhibitors, angiostatin, endostatin, 2-methoxyestradiol, tecogalan, tetrathiomolydate, thalidomide, thrombospondin, prolactin, linomide, tasquinimod, ranibizumab, sorafenib, sunitinib, pazopanib, everolimus. as well as the additional anti-angiogenic agents depicted in table 1 below, or a combination thereof.

TABLE 1

THYROID ANTAGONISTS EXAMPLES

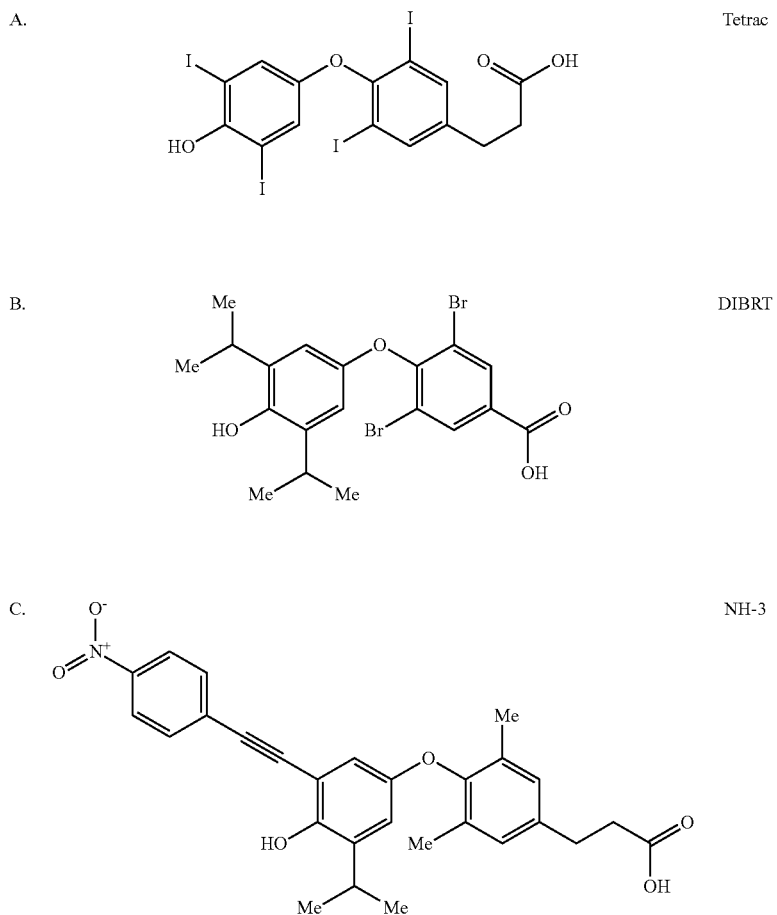

TABLE 1-continued

THYROID ANTAGONISTS EXAMPLES

D.
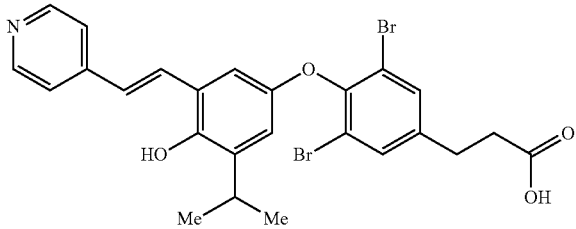 [SMILES: CC(C)c1cc(Oc2c(Br)cc(CCC(=O)O)cc2Br)cc(/C=C/c2ccncc2)c1O]

E.
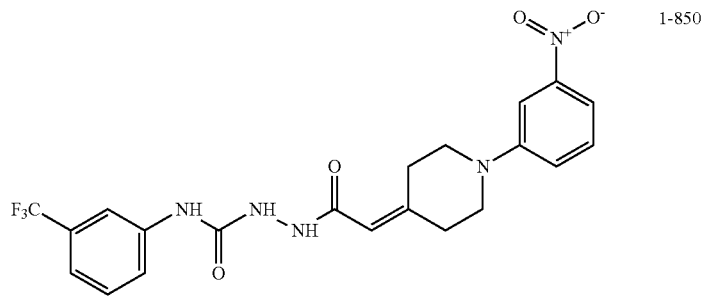
1-850

F.
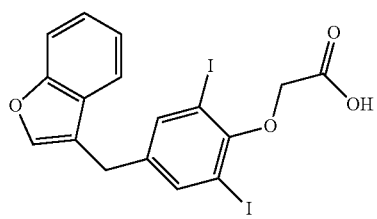 [SMILES: O=C(O)COc1c(I)cc(Cc2coc3ccccc23)cc1I]

G.
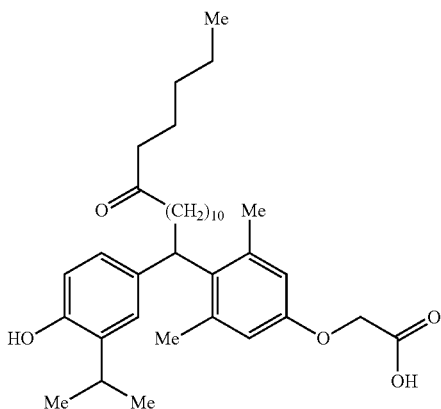

In some embodiments, the anti-angiogenic thyroid hormone antagonists may be conjugated to a polymer. The conjugation between the polymer and the thyroid hormone antagonists may occur via a covalent or non-covalent bond, depending on the polymer being used. In some embodiments, the polymer conjugation may occur through an ester linkage, anhydride linkage, ether linkage or sulfhydryl linkage. In some embodiments, the linkage may include a linker between 3 and 15 atoms long. In alternative embodiments, the linker may be between 3-4, 3-5, 3-6, 3-7 or 3-8 atoms long. The linker between the thyroid hormone antagonists and the polymer may be attached on the outer ring hydroxyl group, in embodiments when the anti-angiogenic agent is an anti-angiogenic thyroid hormone analog. The thyroid hormone antagonists conjugated to a polymer described above may be also referred to as a "conjugated anti-angiogenic agent."

Example 1: Thyroid Hormone Conjugated to a Polymer Via an Ester Linkage

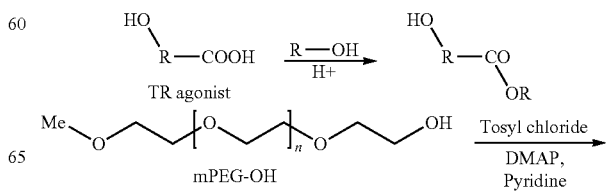

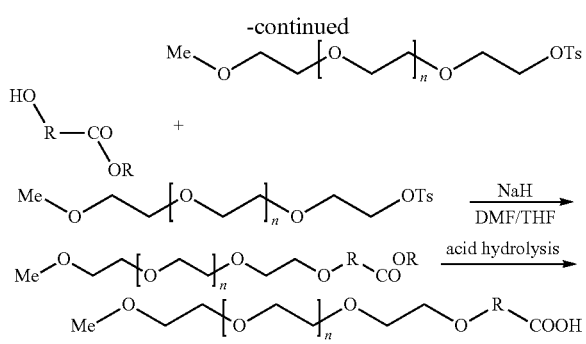

In some embodiments, the polymer that may be conjugated to the thyroid hormone antagonist agent may include but is not limited polyvinyl alcohol, acrylic acid ethylene co-polymer, polyethylene glycol (PEG), methoxypolyethylene glycol-poly(lactide-co-glycolide), polyacrylic acid, polylactic acid, agarose, polyglycolide, polyethylene oxide, m-PEG, polyvinyl alcohol, polyglycolic acid, poly-L-lysine, human serum albumin, carboxymethylcellulose derivatives, carboxyethylcellulose derivatives, carboxyhydroxypropylcellulose derivatives, hyaluronic acid, folate linked cyclodextrin, folate linked dextran, alginate, carrageenan, chitosan, dextran, collagen, polyamine, poly aniline, poly alanine, polytrytophan, poly tyrosine, polylactide-co-glycolide, poly (lactic-co-glycolic) acid (PLGA), polylysyl glycolide, polyglycolide, polylactide, or co-polymers thereof. Embodiments of the polymer conjugations may be used to improve drug viability and improve drug targeting of encapsulated secondary compounds such as chemotherapeutic agents or anti-inflammatory agents that may be targeted to tissues expressing integrin $\alpha v\beta 3$.

Many old and new therapeutics are well-tolerated, however, some compounds may need advanced drug technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain as well as encapsulating additional compounds inside the polymer to control distribution thereof.

For example, in one embodiment, a polymer conjugation may be formed through an ester linkage using polyvinyl alcohol. In this preparation commercially available polyvinyl alcohol (or related co-polymers) may be esterified by treatment with the acid chloride of thyroid hormone analogs, including the acid chloride form. The hydrochloride salt may be neutralized by the addition of triethylamine to form triethylamine hydrochloride which can be washed away with water upon precipitation of the anti-angiogenic thyroid hormone ester polymer form for different analogs.

In an alternative example, a polymer conjugation, through an anhydride linkage using acrylic acid ethylene co-polymer similar to the previous polymer covalent conjugation may be used, however, an anhydride linkage that is derived from reaction of an acrylic acid co-polymer may be formed. This anhydride linkage may be susceptible to hydrolysis in vivo to release the anti-angiogenic agent. Neutralization of the hydrochloric acid may be accomplished by treatment with triethylamine and subsequent washing of the precipitated polyanhydride polymer with water which removes the triethylamine hydrochloride byproduct. This reaction may lead to the formation of an anti-angiogenic agent, acrylic acid co-polymer+triethylamine. Upon in vivo hydrolysis, the anti-angiogenic agent may be released over a time frame that can be controlled and manipulated.

In another alternative embodiment, the polymer may be conjugated to the carboxylic acid or the hydroxyl group of the anti-angiogenic agent as depicted in example 2 and example 3 below.

Example 2: Route of Tetrac/Polymer Conjugates Synthesis Via Carboxylic Acid Group

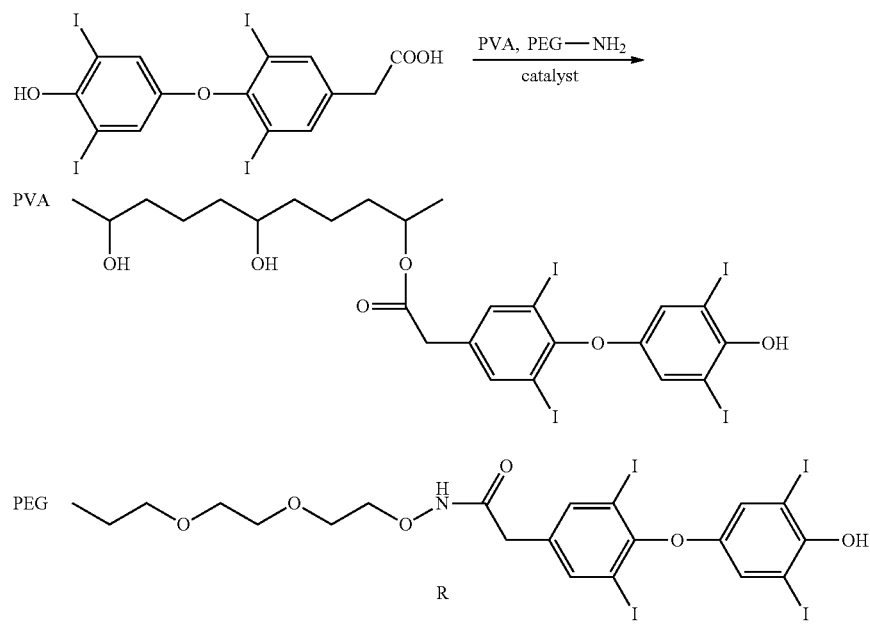

Catalyst: CDI(1,1'-carbonyldiimidazole)
DCC(N,N'-Dicyclohexylcarbodiimide)

Example 3: Route of Tetrac/Polymer Conjugates Synthesis Via Hydroxyl Group

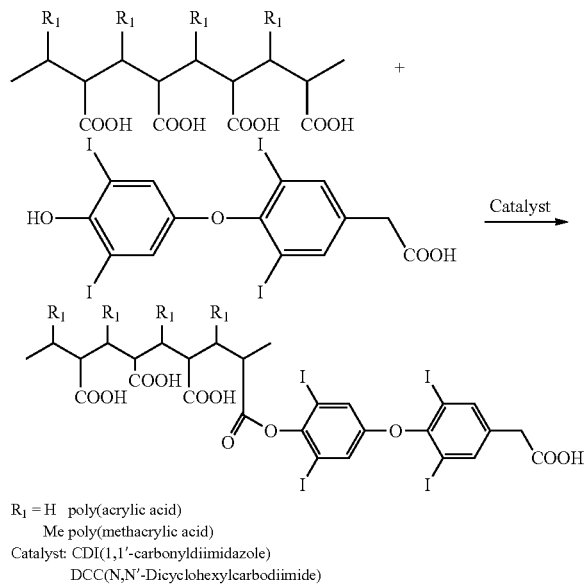

R₁ = H poly(acrylic acid)
  Me poly(methacrylic acid)
Catalyst: CDI(1,1'-carbonyldiimidazole)
  DCC(N,N'-Dicyclohexylcarbodiimide)

In alternative embodiments, a variety of synthetic, natural and bio polymeric side groups with efficient biodegradable backbone polymers may be conjugated to the thyroid hormone analogs. These alternative polymers may include Poly alkyl glycols, polyesters, poly anhydride, poly saccharide, and poly amino acids. Example may include bi-functional PEG, methoxy-PEG, polyvinyl-maleic anhydride, polylactic-co-lysine and polyamidoamine.

Furthermore, in some embodiments, the polymer may be a microparticle or nanoparticle. A microparticle may refer to any particle having a diameter between 0.1 µm and 1000 µm. As used herein, the term "nanoparticle" may refer to particles between approximately 1 nm and less than 1000 nm in diameter. In suitable embodiments, the diameter of the nanoparticles of the present invention may have a particle size having a diameter between approximately 10 nm to <1000 nm. In alternative embodiments, the particle may be less than 500 nm in diameter, or less than about 250 nm in diameter. In certain such embodiments, the nanoparticles of the present disclosure may be between about 10 nm and about 200 nm, between about 30 nm and about 100 nm, or between about 40 nm and about 80 nm in diameter.

In some embodiments of the assay 100, specific strategies for use of the CAM in the context of anti-angiogenesis therapy may include the following: (1) estimation of relapsed patient pro-angiogenic ('anti-angioinhibitory') activity in the absence of tumor grafts in the CAM, when first-line anti-angiogenic treatment has failed or when anti-angiogenesis is being considered as second-line therapy and specific treatment agent activity can be measured in the CAM in the presence of patient serum samples; (2) estimation of host pro-angiogenic activity in standard tumor cell line grafts in the CAM that are relevant to specific, relapsed patients—the assay may also test specific treatment agents; (3) estimation of host pro-angiogenic activity in the presence of biopsied cell grafts from the patient in the CAM, with and without specific anti-angiogenic/chemotherapeutic agent(s).

In some embodiments, the CAM assay may be capable of accepting human tumor xenografts. Moreover, in other embodiments, the CAM assay may not only be capable of accepting human tumor xenografts, but may additionally include a system for testing the patient blood samples in the vasculature of the xenograft. For instance, by using the patient's blood in the vasculature of the human xenograft in the CAM, the assay may be capable of identifying the non-peptide pro-angiogenic thyroid hormone content of the patient's blood, for example the concentrations of T3 or T4.

Studies in myocardium have established that $T_4$, and a thyroid hormone analogue, diiodothyropropionic acid (DITPA) are capable of stimulating coronary arteriolar growth. It has also been shown that the hormone is pro-angiogenic in the CAM model by a cell surface-based mechanism, interacting with the cell surface receptor $\alpha v \beta 3$. Components of the mechanism of angiogenesis may further include transcription of the basic fibroblast growth factor (bFGF) gene and the release of the gene product into the medium of the CAM.

Figure 3:
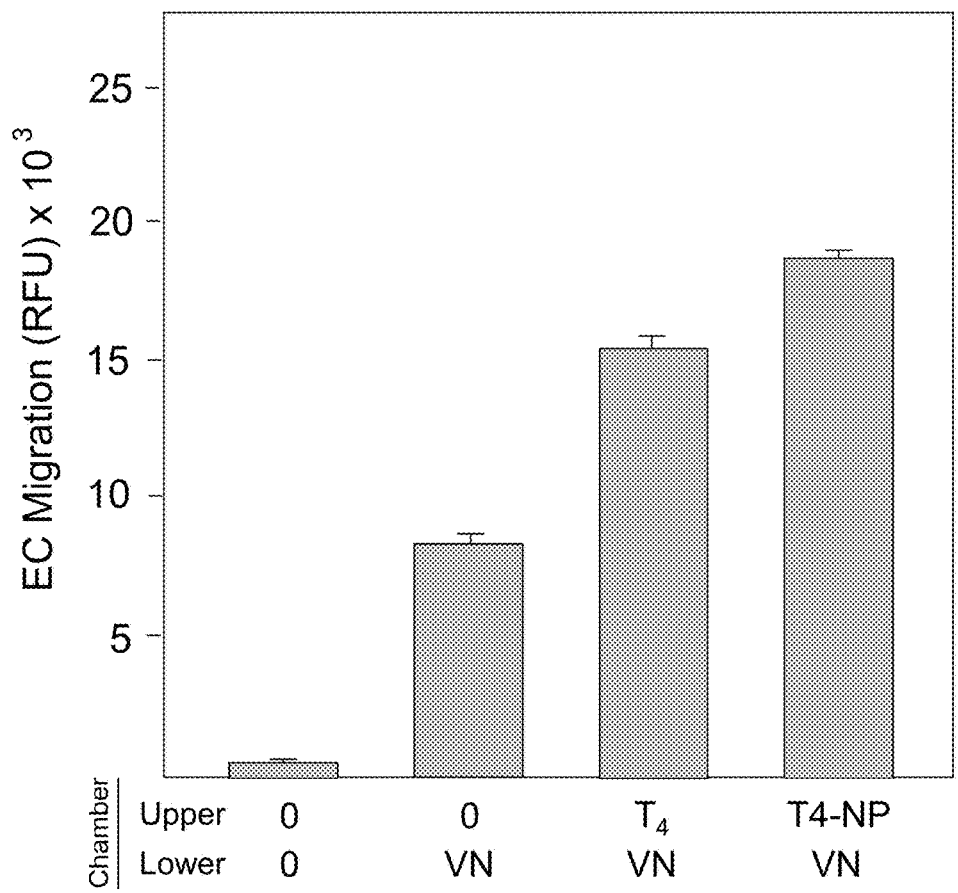
FIG. 3 depicts the effects of $T_4$ and nanoparticulate $T_4$ (T4 NP) on human dermal endothelial cell (EC) migration towards a vitronectin (VN) cue.

The presence of thyroid hormone may also induce microtubule formation by human dermal microvascular endothelial cells. In some instances, the thyroid hormone may stimulate migration of endothelial cells towards a vitronectin cue in a modified Boyden chamber apparatus, as demonstrated in FIG. 3. Vascular microtubule formation is a function of endothelial cell motility and cell-to-cell adhesion. Interference with these endothelial cell functions in the environment of tumors would be therapeutically desirable. Neovascularization around the tumor requires that the intercellular matrix structure of the existing vascular bed be loosened to permit vascular budding and vessel formation. Factors such as angiopoietin-2 (Ang-2) are premonitory contributors to such changes in vascular beds and when paired with VEGF promote angiogenesis. Thrombospondin 1 (TSP1) gene expression is almost invariably suppressed in cancer cells; the gene product is an endogenous anti-angiogenic factor. Relief of suppression of transcription of TSP1 is desirable in chemotherapy. While it is feasible to block vascular growth receptor function with monoclonal antibody to specific receptors or by interference with crosstalk between integrin $\alpha v \beta 3$ and vascular growth factor receptors clustered with the integrin, it would also be desirable to decrease specific vascular growth factor receptor gene expression or local cancer cell release of just-synthesized protein growth factors. A few inhibitors of vascular growth factors or their receptors that are currently available do interfere with the actions of more than one growth factor or angiogenesis-relevant protein. Ziv-aflibercept complexes with VEGF-A/VEGF-B and placental growth factor (PlGF) and tyrosine kinase inhibitors such as sunitinib, may affect activities of both VEGF and PDGF.

Embodiments of the CAM assay may further suggest that thyroid hormone may also influence the activities of vascular endothelial growth factor (VEGF) and platelet-derived growth factor (PDGF). That is, a pharmacologic inhibitor of thyroid hormone action at the $\alpha v \beta 3$ receptor may be capable of decreasing the pro-angiogenic actions of VEGF and PDGF in the CAM. Such a mechanism is may involve crosstalk between integrin $\alpha v \beta 3$ and the adjacent receptors for VEGF, PDGF and bFGF on the cell surface. It is also clear that thyroid hormone may also modulate certain non-angiogenic functions of the plasma membrane receptors for epidermal growth factor (EGF) and insulin-like growth factor-1 (IGF-1) [37]. EGF and IGF-1 have pro-angiogenic properties that are important for determining the presence of crosstalk between receptors for these growth factors and the iodothyronine receptor on αvβ3.

Examples of the CAM assay methodology may include the step of providing chick embryos. In some embodiments, the chick embryos may be approximately 10 days old. The chick embryos may be incubated at approximately 37° C. with approximately 55% relative humidity. A hypodermic needle may be used to make a small hole in the shell concealing an air sac, and a second hole may be made on the broad side of the egg, directly over an avascular portion of the embryonic membrane. A false air sac may be created beneath the second hole by the application of negative pressure at the first hole, causing the CAM to separate from the shell. A window, approximately 1.0 cm$^2$, in size may be cut in the shell over the CAM with a small-crafts grinding wheel, allowing direct access to the underlying CAM.

In some embodiments, a pro-angiogenic agent may be provided to induce new blood vessel branches on the CAM of 10-day-old embryos. In the exemplary embodiment, the pro-angiogenic agents may be the endogenous non-peptide pro-angiogenic hormones supplied in the patient's blood sample. The patient's blood sample may subsequently be introduced into the xenograft having a vasculature system in the CAM. The pro-angiogenic agent, the blood or serum sample of the patient along with one or more anti-angiogenic agents may be applied to a sterile disk and followed by allowing the disks to dry. In some embodiments of the CAM assay, Sterile disks of No. 1 filter paper (Whatman International) may be pretreated with approximately 3 mg/mL cortisone acetate and 1 mmol/L of the patient's blood or serum, along with one or more anti-angiogenic agents and air dried under sterile conditions. The disks may then be suspended in phosphate buffered saline (PBS) and placed on growing CAMs. At approximately the 24 hour mark, a mitogen-activated protein kinase (MAPK) cascade inhibitor such as PD 98059 may also be added to CAMs topically by means of the filter disks. Exemplary embodiments having one or more anti-angiogenic agent, may include two, three, four, five or more anti-angiogenic agents, including at least one thyroid hormone antagonist such as tetrac, triac, or conjugated tetrac or triac.

After incubation at 37° C. with 55% relative humidity for 3 days, the CAM tissue directly beneath each filter disk may be resected and treated. The tissues may subsequently be washed approximately three times with PBS, placed in 35-mm Petri dishes (Nalge Nunc), and examined under a stereomicroscope at approximately 50× magnification or more. Digital images of CAM sections exposed to filters may be collected and quantified using a 3-charge-coupled device color video camera system and analyzed with Image-Pro software (Media Cybernetics) or equivalent software. Embodiments of the CAM system may not only index tumor-related angiogenesis, but permits spherical tumor growth of the implanted cells. Spherical growth may be important to the development of a hypoxic cell population that resemble tumor behavior clinically. Aggressive xenograft behavior in the CAM model may include metastasis to the chick embryo in the system.

Figure 2:
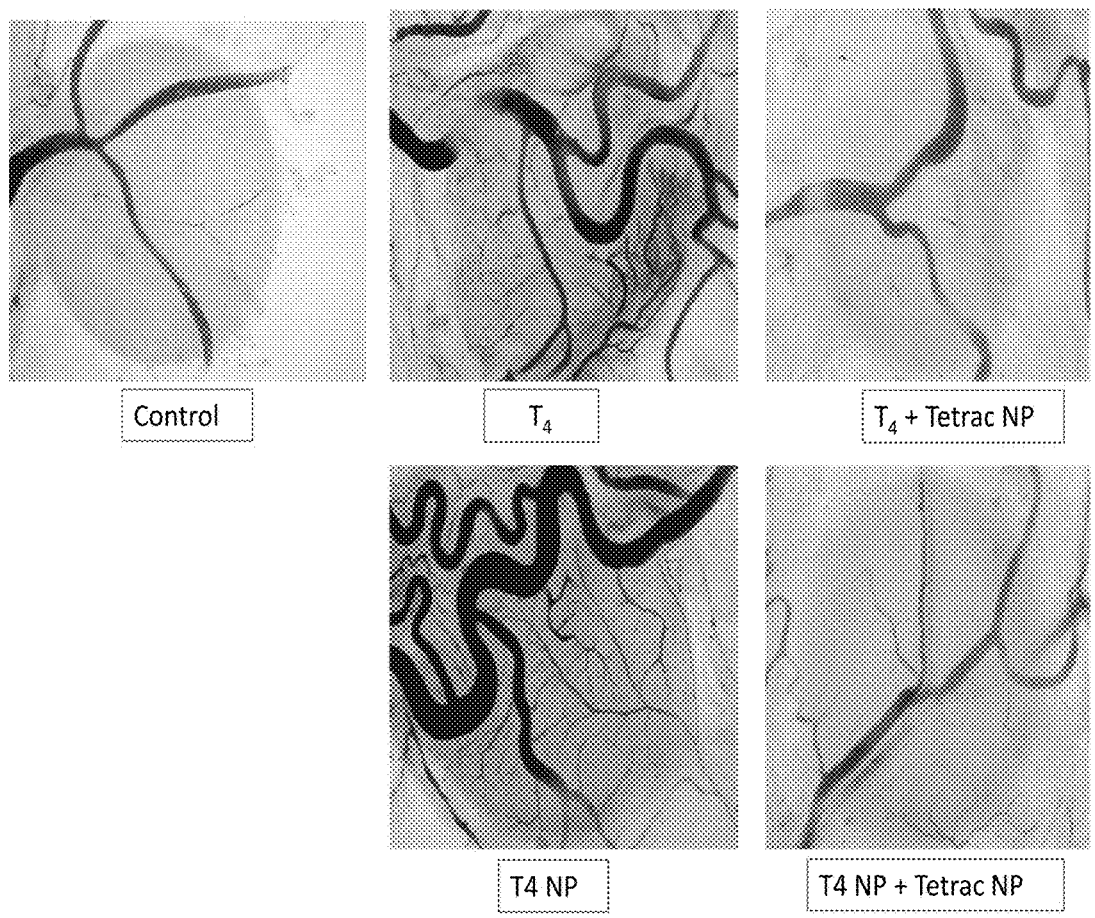
FIG. 2 depicts angiogenic activities of thyroid hormone ($T_4$), nanoparticulate $T_4$ (T4 NP) and nanoparticulate tetrac (tetrac NP) in the chick chorioallantoic membrane (CAM) model.

The CAM assay results shown in FIG. 2 depict the activities of pro-angiogenic agents thyroid hormone ($T_4$) and nanoparticulate $T_4$ (T4 NP) as well as the anti-angiogenic agent, conjugated nanoparticulate tetrac (tetrac NP) in the chick chorioallantoic membrane (CAM) assay. It should be noted that the nanoparticulate formulations cannot enter the cell due to the size of the conjugated polymers preventing access across the cell membrane. Based on the results depicted in the figure, the pro-angiogenic actions of $T_4$ and T4 NP are similar in magnitude, indicating initiation of the effects at integrin αvβ3 on the cell surface. Moreover, it can be seen that tetrac NP eliminates the vascular activities of $T_4$ and T4 NP.

Subsequently, after the step of performing the CAM Assay 104 using the blood sample collected 102 from the patient, the resulting blood vessel formation of the CAM results may be quantified 106. The step of quantifying 106 the vessel branch points that formed during the CAM assay allows the doctor or clinician to evaluate the presence of pro-angiogenic hormones in the patient's blood or serum sample and determine whether or not resistance to angioinhibition has developed. For example, if a CAM performed in the presence of a single anti-angiogenic agent has an increased number of vessel branches compared with a CAM performed in the presence of the same anti-angiogenic agent and a thyroid hormone antagonist, the CAM results may indicate that the elevated levels of thyroid hormone such as free T4, may be the cause of an increase in angioinhibition resistance thus preventing or limiting the effects of the anti-angiogenic agent administered alone.

Figure 4:
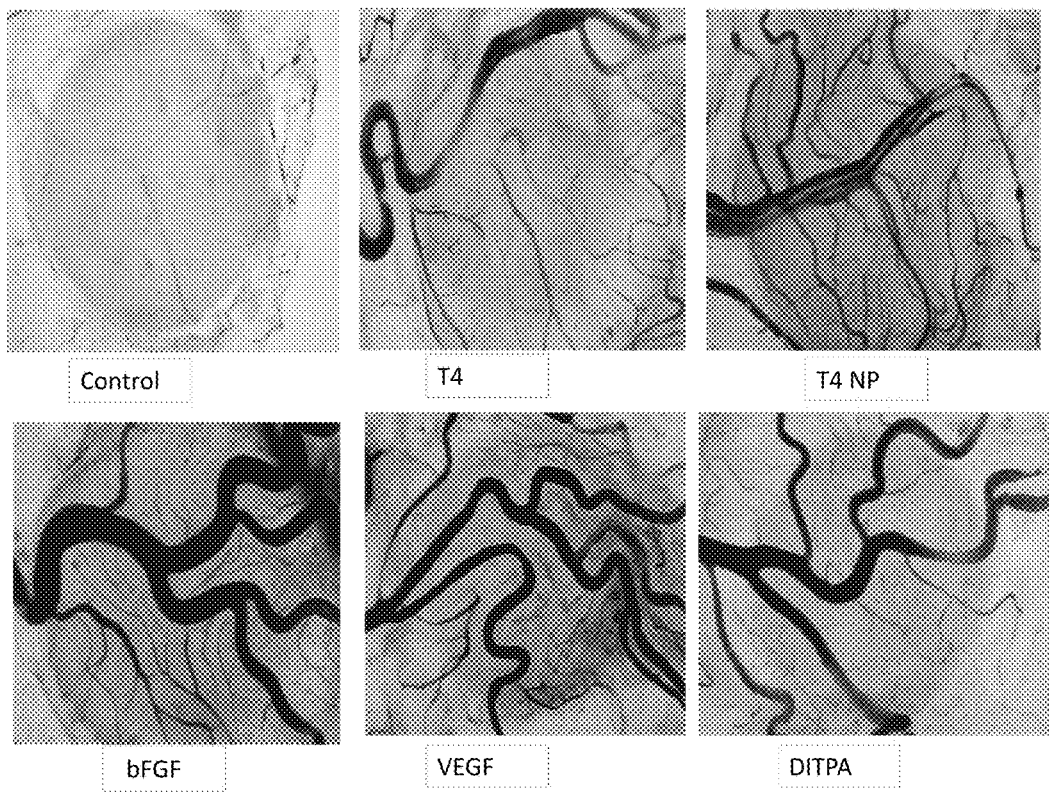
FIG. 4 depicts results of a chick chorioallantoic membrane (CAM) assay demonstrating the angiogenic activity of L-thyroxine ($T_4$), nanoparticulate $T_4$ (T4 NP), basic fibroblast growth factor (bFGF), vascular endothelial growth factor (VEGF) and diiodothyropropionic acid (DITPA), and a phosphate-buffered saline (control).

FIG. 4 depicts the results of an embodiment of the Chick Chorioallantoic Membrane (CAM) assay identifying angiogenic activity of L-thyroxine ($T_4$), nanoparticulate $T_4$ (T4 NP), bFGF, VEGF and diiodothyropropionic acid (DITPA), a thyroid hormone analogue. FIG. 4 provides a visual depiction of the CAM assay results. The results demonstrate a quantification of the vascular branch points, providing an indication of angiogenic capabilities of each hormone or angiogenic agent present in the tested samples. The step of quantifying 106 the vessel branch points in the CAM system may be performed in some embodiments by analysis with standardized software of digitized images permitting statistical evaluation of possible pro-angiogenic effects endogenous pro-angiogenic, non-peptide hormones and growth factors present in the patient's sample.

Following the assay 100 step of quantifying 106 the vessel branch points developed during the CAM assay, the clinician or doctor performing assay 100 may proceed in the step of identifying 108 the presence of elevated endogenous pro-angiogenic hormone or growth factor levels, in view of the CAM results as well as whether the elevated levels are reducing or limiting the effectiveness of subsequently administered anti-angiogenic agents. For example, the step of identifying the elevated levels of pro-angiogenic hormones and growth factors may be accomplished by statistically comparing various CAM results, including pro or angiogenic activities of biological fluids such as blood or serum, one or more pharmaceutical agents such as an anti-angiogenic agent and one or more endogenous growth factors. For example, CAMs may be performed using the patient blood samples having unknown concentrations of endogenous hormones and growth factors, in conjunction with CAMs exposed to samples having known standards and quantified concentration levels of pro-angiogenic hormones and growth factors. Using a statistical analysis software, the unknown patient concentrations may be identified by comparing the CAM results with CAM results of the various known standards. For example, one or more standards may be prepared using known concentrations of the previously described pro-angiogenic hormones such as T4, T3, DITPA, and endogenous growth factors such as bFGF, VEGF or platelet derived endothelial growth factor (PDGF). A comparison between the branch points of the various known standards and the unknown patient sample may be used to assist the clinician in identifying the concentrations of hormone or growth factor present. Quantitation of vascular branch points in the CAM permits comparison of effectiveness of different agents or of concentrations of single agents. In the typical case where angioinhibition resistance has not been developed, each of the substances included in the Table 2 below depict the pro-angiogenic properties of each hormone or factor being markedly diminished by Nanotetrac (NT). In a CAM using a sample having developed resistance, the branch points may not demonstrate diminishment in the presence of an anti-angiogenic agent. However if there is diminishment of branch vessels when the CAM is performed in combination with NT and an anti-angiogenic agent, it may be concluded that the culprit of the diminished effect of the anti-angiogenic agent is the presence of the endogenous pro-angiogenic hormones.

TABLE 2

Inhibition of activities of pro-angiogenic factors in the CAM assay by Nanotetrac (NT) (2 µg/CAM)

| Treatment | Branch points ± SEM |
|---|---|
| PBS control | 75.6 ± 7.3 |
| Void PLGA nanoparticle | 76.8 ± 11.1 |
| $T_3$ (6.5 ng/mL) | 186.8 ± 16.4 |
| $T_3$ + NT | 110 ± 8.1 |
| $T_4$ (100 nM) | 119.2 ± 15.6 |
| $T_4$ + NT | 67.1 ± 10 |
| LPS (5 µg/mL) | 106 ± 9.3 |
| LPS + NT | 70.5 ± 2.9 |
| Bradykinin (5 µg/mL) | 106.7 ± 4.8 |
| Bradykinin + NT | 62 ± 12.5 |
| Angiotensin II (5 µg/mL) | 103.2 ± 25.9 |
| Angiotensin II + NT | 70.8 ± 10.3 |
| VEGF (2 µg/mL) | 182.4 ± 8.4 |
| VEGF + NT | 127.0 ± 12.7 |
| bFGF (1 µg/mL) | 184.6 ± 18.5 |
| bFGF + NT | 111.5 ± 9.8 |
| bFGF + VEGF + TNF-α | 282.4 ± 8.4 |
| bFGF + VEGF + TNF-α + NT | 132.4 ± 17.8 |

Moreover, in some CAMs, the CAM may be performed using the patient sample in the presence of the anti-angiogenic agent, and even in the presence of chemotherapeutic agents. The development of resistance to angioinhibition can be identified and quantified, based on an evaluation of the vessel branch points formed and in some embodiments by comparing vessel branch points in CAMs of the patient sample exposed to an anti-angiogenic agent and ones that were not exposed to the agent. For instance, it would be expected that a CAM that was exposed to an anti-angiogenic agent would develop significantly less branch vessel branch points than a CAM that was not exposed to the anti-angiogenic agent. If by comparison, there is a statistically significant amount, or similar amount of vessel branch points in the CAM treated with the anti-angiogenic agent, a determination that resistance to angioinhibition may have developed might be concluded.

In some embodiments, the step of identifying 108 whether or not the patient's blood or serum sample possesses elevated levels 110 of endogenous non-peptide pro-angiogenic hormone or growth factors may further assist the doctor or clinician in prescribing a treatment. For instance, if the assay 100 is performed and elevated levels of the endogenous non-peptide pro-angiogenic hormone or growth factors are not identified, the clinician or doctor may continue to prescribe traditional disease therapy, which may consist of administering 114 an anti-angiogenic agent. In other embodiments of the method, in particular where elevated levels of endogenous non-peptide pro-angiogenic hormone or growth factors are identified, and/or the patient is identified to have developed resistance to angioinhibition, the doctor or clinician may proceed to reduce the resistance by first inducing 112 subclinical hypothyroidism in the patient followed by administering 116 one or more anti-angiogenic agents. Subclinical hypothyroidism may refer to an individual or patient having reduced thyroid hormone production or conversely elevated thyroid stimulating hormone (TSH) concentrations that are greater than the upper limits of the normal ranges depicted in Table 3 below, but not high enough in concentration for the patient to develop the symptoms or clinical effects associated with hypothyroidism.

The anti-angiogenic agents may be administered with one or more pharmaceutically acceptable carriers. "Pharmaceutically acceptable carriers" may refer to and include any and all solvents, dispersion media, coatings, antibacterial and antifungal agents, isotonic and absorption delaying agents, and the like which are compatible with the activity of the agent and are physiologically acceptable to the subject. An example of a pharmaceutically acceptable carrier may be buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

The anti-angiogenic agent may be formulated for administration via one or more of the following routes, including but not limited to parenteral including via catheterization, oral, rectal, topical such as a Band-Aid or a gauze pad, ophthalmic, local implantation, subcutaneous, intramolecular, intraperitoneal, intramuscular, buccal, vaginal, intraorbital, intracerebral, intracranial, intra-spinal, interventricular, intrathecal, intracisternal, intracapsular, intranasal or by aerosol administration or a combination of routes thereof. For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

In some embodiments, an anti-angiogenic agent having a polymer or nanoparticle polymer may further include one or more anti-inflammatory agents encapsulated by the polymer. For example, in some embodiments, the anti-inflammatory agent may be adsorbed to the polymer encapsulating it. The conjugated anti-angiogenic agent may deliver the anti-inflammatory agent locally to the site of inflammation as the anti-angiogenic portion of the conjugated anti-angiogenic agent targets the integrin receptor αvβ3. For example, a tetrac moiety covalently bound to a PLGA polymer may be used as a ligand of αvβ3, expressed by rapidly dividing endothelial cells at the sites of inflammation. The anti-inflammatory agent may be encapsulated by the PLGA particle, thus as the tetrac selectively targets and seeks out the αvβ3 bearing endothelial cells, the PLGA nanoparticle may release the anti-inflammatory agent locally right at the point of inflammation.

The control of inflammation and the targeting may be particularly useful in treating diseases known for having a portion of the disease's known effects attributed to inflammation. Such diseases may include arthritis, Parkinson's diseases, and Alzheimer's disease. The integrin αvβ3 may be generously or overly expressed by tumor cells and dividing blood vessel cells. As disclosed above, thyroid hormones such as tetrac and triac may bind exclusively to the αvβ3 integrin receptor, making the thyroid hormone of the conjugated thyroid hormone analog a selective targeting mechanism for tumor cells which express the integrin receptor. Furthermore, conjugated thyroid hormone analogues or other ligands of αvβ3 may have significant potential either alone or in combination with other anti-inflammatory agents because integrin αvβ3 is present on plasma membranes of the cells relevant to the formation of inflammation. For example, integrin αvβ3 may be found on the plasma membrane of neutrophils, peripheral blood lymphocytes, and alveolar macrophages at the sites of lung inflammation.

The early inflammatory component of the innate immune response may include contributions from inflammatory cells, response-modifying cytokines and chemokines and blood vessel growth factors. Anti-angiogenic agents such tetrac and conjugated tetrac nanoparticles may block contributions to the pro-angiogenic component of inflammation via actions on interleukins as well as by decreasing the expression of cytokine and chemokine mRNA. Vascular endothelial growth factor (VEGF), basic fibroblast growth factor (bFGF), platelet-derived growth factor (PDGF), insulin-like growth factor-1 (IGF-1) and EGF are factors that have all been implicated in the vascular phase of the inflammatory response. Acting via the receptor on integrin αvβ3, conjugated tetrac and other conjugated thyroid hormone analogs, may block the pro-angiogenic actions of each of these factors.

Furthermore, in some instances, crosstalk between the tetrac-thyroid hormone receptor on integrin αvβ3 and estrogen receptor-α (ERα) may exist in human lung carcinoma cells that express this estrogen receptor. The proliferative effect of thyroid hormone at αvβ3 in such cells may be dependent upon ERα. This observation raises the possibility that the actions of thyroid hormone and anti-angiogenic agents on inflammation that are mediated by their receptor on integrin αvβ3 may be involved with other non-peptide hormone response systems that may be regulated at the cell surface.

The encapsulated anti-inflammatory agents within the polymer may be selected from non-steroidal anti-inflammatory drugs (NSAIDS), salicylates, anti-inflammatory glucocorticoids, pirfenidone or a combination of anti-inflammatory agents thereof. An NSAID may be any group of anti-inflammatory and analgesic drugs that may suppress inflammation and pain by inhibiting the cyclooxygenase pathway and preventing release of inflammatory mediators (e.g. prostacyclin, prostaglandins and thromboxane). NSAIDs may bind to cyclooxygenase-1 (COX-1), cyclooxygenase-2 (COX-2) or a combination of COX inhibitors. In some embodiments, the NSAIDS encapsulated within the polymer of the conjugated thyroid hormone analog may include but is not limited to ibuprofen, diclofenac, diclofenac with misprostol, indomethacin, ketoprofen, fenbrufen, naproxen, sulindac, celecoxib, nabumetone, mefenamic acid, oxyphenbutazone, diflunisal, etodolac, fenoprofen, flurbiprofen, meclofenamate, meloxicam, nabumetone, oxaprozin, piroxicam, tolmetin, valdecoxib and propionic acid derivatives.

In another embodiment, the anti-inflammatory agent may include one or more salicylates encapsulated by the polymer of the conjugated thyroid hormone analogue. A salicylate may be a salt or ester of salicylic acid ($C_6H_4(OH)COOH$). Salicylates may have an OH group in the ortho position to the carboxyl group. In some instances, a salicylate may be referred to as 2-hydroxybenzoic acid. Salicylates may include one or more of the following compounds encapsulated inside the polymer of the conjugated thyroid hormone analog, including but not limited to aspirin, choline salicylate, choline, magnesium salicylate, and sodium salicylate.

Embodiments of the anti-angiogenic agents comprising one or more anti-inflammatory glucocorticoids may include one or more of the following compounds encapsulated by the polymer of the conjugated anti-angiogenic agent. A glucocorticoid may be any corticoid substance that increases gluconeogenesis and may raise the concentration of glycogen in the liver and blood glucose. An anti-inflammatory glucocorticoid may be any glucocorticoid that has an effect on the inflammation response by the body, for example by inhibiting the release of histamine. Said anti-inflammatory glucocorticoids may include, but are not limited to hydrocortisone, cortisone, cortisol, dexamethasone, dexamethasone Intensol™, budesonide, methylprednisolone, prednisolone, prednisolone sodium phosphate and prednisone.

In some embodiments, the anti-inflammatory agent being encapsulated by the polymer may include anti-fibrotic agents having anti-inflammatory properties. An anti-fibrotic may be an agent that causes the regression of fibrosis. An example of an anti-fibrotic agent with anti-inflammatory effects may include pirfenidone, NOS-2, daidzein, sirolimus and tyrosine kinase inhibitors including nintendanib.

In some embodiments, the polymer of the conjugated anti-angiogenic agent may further include encapsulated antioxidant polyphenols inside the polymer for local release at the site of inflammation. A polyphenol may refer to a compound containing one or more phenolic hydroxyl groups. An anti-oxidant polyphenol may be a polyphenol that prevents or inhibits oxidation or reactions promoted by oxidants, such as oxygen, peroxide or free radicals. The anti-oxidant polyphenol may include one or more flavones, isoflavones and/or flavonoids such as resveratrol, quercetin, myricetin, catechin, epigallocatechin, enistein and combinations thereof.

In yet another embodiment, the polymer may encapsulate one or more additional agents to release at the anti-angiogenic agent's target binding site, integrin αvβ3. One or more additional agents that may be encapsulated within the polymer may include, but is not limited to, bisphosphonates such as risendronate, alendronate, ibandronate, etidronate, pamidronate, tiludronate, and zoledronic acid, growth factors, hormones, enzymes, antibiotics, vasodilators, anti-coagulants, anti-virals, anti-bacterials, immuno-suppressants, analgesics, vascularizing agents, or cell adhesion molecules, or combinations thereof or other bioactive agents.

In addition to the aforementioned ingredients, formulations of the conjugated anti-angiogenic agent may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants), excipients, dispersing agents; inert diluents, granulating and disintegrating agents, sweetening agents, coloring agents, physiologically degradable compositions such as gelatin; aqueous vehicles and solvents; oily vehicles and solvents; dispersing or wetting agents; emulsifying agents, demulcents, buffers, salts, fillers, emulsifying agents, antioxidants, antibiotics, antifungal agents, stabilizing agents, and pharmaceutically acceptable polymeric or hydrophobic materials and the like.

Embodiments of anti-angiogenic agents such as conjugated thyroid hormone analogs may further express selective anti-inflammatory effects toward chemokine receptors and chemokine ligand gene expression. For example, studies were performed measuring the effects of conjugated tetrac on tumor cell expression of the mRNA of the chemokine ligand CX3CL1 (also known as "fractalkine") and the mRNA of its CX3CR1 receptor for fractalkine. Fractalkine may mediate chemotaxis and adhesion of inflammatory cells via its receptor. Furthermore, fractalkine may be considered a pharmacologically high priority anti-inflammatory target, because fractalkine may participate in the early inflammatory components of several neurodegenerative diseases, including Alzheimer's disease, Parkinson's disease and HIV-associated encephalopathy.

In other embodiments, the anti-angiogenic agent may further comprise one or more chemotherapeutic agents encapsulated inside the polymer formulation of the conjugated anti-angiogenic agent. Examples of a chemotherapeutic that may be encapsulated and specifically targeted to a tumor using the integrin $\alpha v \beta 3$ receptor site of the anti-angiogenic agent, may include doxorubicin, etoposide, cyclophosphamide, 5-fluorouracil, cisplatin, trichostatin A, paclitaxel, gemcitabine, taxotere, carboplatinum, irinotecan, topotecan, adriamycin, bortezomib, and temzolomide. In an alternative embodiment, the chemotherapeutic agent may be co-administered with the anti-angiogenic agent.

Endogenous circulating hormones such as thyroid hormone may clinically oppose the anti-angiogenic chemotherapy of cancer in patients. The levels of hormone, in particular, T4/free T4, may be sufficiently high in certain cancer patients to blunt the effect of therapy specifically directed at one or several vascular growth factors and thus limit the anti-tumor effectiveness of the therapeutic agent. In some embodiments, it may be desirable to reduce the levels of endogenous pro-angiogenic hormones such as $FT_4$, $T_4$, and $T_3$ using an anti-thyroid agent to decrease the patient's production of these proangiogenic hormones and conversely though a negative feedback loop, raising the levels of the patient's TSH levels.

In the clinical setting, other paradigms may be considered for evaluating and identifying the potential contribution of endogenous pro-angiogenic hormones, such as thyroid hormone, to the impact of therapeutic angioinhibition. In the absence of anti-angiogenic therapy, it may also be useful to quantitate the contribution of endogenous thyroid hormone to tumor vasculature. This strategy may involve estimation histologically of the ratio of tumor vascularity:tumor cellularity in biopsies from hypothyroid vs. euthyroid cancer patients or between different collected samples. Embodiments of these measurements may include free T4 levels at the times of biopsy.

Cancer, tumors and other disease previously described including Parkinson's disease and Alzheimer's disease may behave differently in the setting of hypothyroidism, whether spontaneous or induced, than in euthyroidism. In each of these settings, desirable clinical behavior may accompany decreased circulating levels of endogenous pro-angiogenic hormone (such as thyroid hormone) and this may in part reflect actions of the pro-angiogenic hormone on angiogenesis. In some embodiments subclinical hypothyroidism may be medically-induced by administering an anti-thyroid agent. An anti-thyroid agent may be any agent capable of reducing the release of thyroid hormones such as FT4, T4, and T3 into the rest of the patient's body. Suitable anti-thyroid agents may include carbimazole, methimazole, propylthiouracil (PTU), or potassium perchlorate. The decreasing thyroid hormone levels of the patient may initiate a negative feedback loop mechanism to increase the overall production of the circulating TSH. The normal range for circulating TSH may be between approximately 0.3-3.04 mIU/L, where IU is the designation for international units. TSH levels may be monitored by the clinician or doctor as an index of the drop in thyroid hormones. In the exemplary embodiment, it has been found that the anti-thyroid agent may be administered in a sufficient dose to reduce the endogenous thyroid hormone production and thus elevate TSH, to levels equal to or beyond the upper threshold (3.04 mIU/L or 4.70 μIU/mL) of the normal range, provided in table 3. In the some embodiments, the clinician may continue to track TSH levels and discontinue the administration of the anti-thyroid agent prior to the patient developing symptoms or the clinical effects of hypothyroidism.

In some embodiments, the reduction in thyroid hormone as evidenced by the elevating TSH levels, has been effective in increasing the effectiveness of anti-angiogenic agents, thus contributing to arresting the progression and increasing overall survival in patients suffering from the diseases listed above, including unexpectedly in glioblastoma patients. In other embodiments, particularly in the cancer-relevant context, it should also be pointed out that some pro-angiogenic hormones such as thyroid hormone are anti-apoptotic, which is capable of supporting survival of the cancer cell and its angiogenic activity. The hormone has been shown to inhibit apoptosis induced in vitro by specific agents such as resveratrol and ceramide. By suppressing thyroid hormone, which is evidenced by the elevating TSH levels, the survivability and anti-apoptotic effects of the thyroid hormone may be diminished, thus making the cancerous cells more vulnerable and treatable.

In some embodiments, such as in the case of thyroid hormone, elevated circulating concentrations of free $T_4$ ($FT_4$) may be encountered transiently or longer in a non-thyroidal illness (NTI) syndrome or in patients receiving high-dose $L-T_4$ replacement. The NTI syndrome may include low serum $T_3$ concentration and suppressed TSH. In the setting of the NTI, reducing the circulating levels of T3 and TSH may not be germane to angiogenesis but rather supports the conclusion that elevated $FT_4$ is acting as the underlying cause of the NTI, and should thus be reduced. In some patients, elevated endogenous $FT_4$ wherein the $FT_4$ is within the upper quartile or higher of the reference range lying between approximately 0.8-1.8 ng/L, may demonstrate a resistance to angioinhibition. In some embodiments, acute reductions in circulating endogenous thyroid hormone may be initiated to reduce the resistance to angioinhibition, because established hypothyroidism will result in arrested tumor cell proliferation and decreased release of vascular growth factors. These factors will reduce detectability of anti-angiogenic activity of an added pharmaceutical or biological agent, such as a subsequently administered anti-angiogenic agent. In other embodiments, tyrosine kinase inhibitors may be administered because they may also employ a side effect of incidentally inducing hypothyroidism in a patient. Tyrosine kinase inhibitor induced hypothyroidism may be particularly useful in effecting vascular tumors and renal cell carcinoma.

In some embodiments, as described above, levels of T4 greater than or equal to the upper quartile of the biologically normal $T_4$ range may be sufficient to depress circulating TSH ('subclinical hyperthyroidism') and may be adequate to oppose pharmacologic angioinhibition by multiple mechanisms. By inhibiting production of thyroid hormone, using an anti-thyroid agent, identifiable by observing a rise in the serum TSH to the upper limit of the reference range (0.5-4.70 μIU/mL, 0.3-3.04 mIU/L) or above, but avoiding clinical symptoms of hypothyroidism, will reduce the opposition of angioinhibition resistance. The reference range of normal concentrations of TSH may be found in table 3 below. In one embodiment of this method, decreasing the production of thyroid hormone to induce hypothyroidism has been done systematically in the setting of end stage glioblastoma multiforme, a highly vascular tumor, with reasonable success. In another embodiment, inducing hypothyroidism appears to have changed the course of breast cancer, reducing the aggressiveness of the disease.

In some embodiments, the assay 100 may further include additional treatment that may be administered after the step of inducing subclinical hypothyroidism. The assay 100 may further comprise the step of administering to the patient, an anti-angiogenic agent, an anti-angiogenic agent encapsulating a chemotherapeutic agent, an anti-angiogenic agent encapsulating an anti-inflammatory agent, or a combination of compounds thereof as described above.

In an alternative embodiment of the assay depicted in FIG. 1, the development of resistance to angioinhibition may be treated prophylactically, before host resistance actually develops. Examples of diseases susceptible to anti-angiogenic compounds which may benefit from prophylactically preventing the development of resistance to angioinhibition may include primary or metastatic tumors, adenoid carcinoma, breast cancer, kidney cancer, colon cancer, glioblastoma multiforme, head-and-neck cancer, hepatoma, lung cancer, lymphoma, melanoma, basal cell carcinoma, squamous cell carcinoma, myeloma, neuroblastaoma, ovarian cancer, prostate cancer, pancreatic cancer, renal cancer, carcinoma, stomach cancer, thyroid cancer, diabetic retinopathy, wet macular degeneration, arthritis, Parkinson's Disease, Alzheimer's Disease or a combination of diseases thereof.

Embodiments of a method for prophylactically treating the development of host resistance to angioinhibition may follow one or more of the steps outlined in assay 100. In the alternative embodiment, the step of quantifying and identifying the endogenous pro-angiogenic hormones of the patient blood or serum sample may reveal normal concentration ranges of the pro-angiogenic hormones, such as free T4 which may have a normal concentration of approximately 0.8-1.8 ng/L or in SI units, 10-23 pmol/L. Other standard ranges of pro-angiogenic hormones are provided in Table 3 below. Subsequently, the method may include the step of inducing subclinical hypothyroidism (as described above) in the patient while the patient is still exhibiting pro-angiogenic hormone levels within the normal concentration range and/or not demonstrating angioinhibition resistance in a CAM assay. Moreover, embodiments of the prophylactic method may start, continue, or resume treating the patient's disease or condition by administering to the patient an anti-angiogenic agent. In some embodiments, the anti-angiogenic agent may be any agent that is capable of binding to the integrin αvβ3. The anti-angiogenic agent may further include an anti angiogenic agent that binds to integrin αvβ3 encapsulating a chemotherapeutic agent, an anti-angiogenic agent that binds to integrin αvβ3 encapsulating an anti-inflammatory agent or a combination of agents thereof, as described previously in the exemplary embodiment of the assay 100.

TABLE 3

Normal Concentration Range of Endogenous Hormones

| Hormone or Growth Factor | Concentration (Conventional Units) | Concentration (SI Units) |
| --- | --- | --- |
| $T_3$ (Triiodothyronine) Free | 0-6 years: 2.4-4.2 pg/mL<br>7-17 years: 2.9-5.1 pg/mL<br>>18 years old: 2.3-4.2 pg/m | 3.5-6.5 pmol/L |
| $T_3$ (Triiodothyronine) Reverse (RT3) | Birth-6 days: 600-2500 pg/mL<br>>7 days old: 90-350 pg/mL | Adults: 0.11-0.32 ng/ml<br>0.04-0.29 nmol/L |
| $T_3$ (Triiodothyronine) Total | Cord blood: 14-86 ng/dL<br>1-7 days: 100-470 ng/dL<br>8-364 days: 105-245 ng/dL<br>1-9 years: 94-269 ng/dL<br>10-19 years: 102-200 ng/dL<br>>20 years old: 80-200 ng/dL | Adults: 0.8-2.0 ng/ml<br>0.9-2.8 nmol/L |
| $T_4$ (thyroxine) Free | 0.8-1.8 ng/L | 10-23 pmol/L |
| $T_4$ (thyroxine) Total | 4.5-12.5 µg/dL | 58-161 nmol/L |
| Thyroid-stimulating hormone (TSH) | 0.5-4.70 µIU/mL<br>0.3-3.04 mIU/L.<br>(American Association of Clinical Endocrinologists guidelines) | 0.5-4.70 mIU/L |
| Progesterone | Male:<br>0.3-1.0 ng/mL | Female:<br>0-8 days: 0-8 ng/mL<br>9 days-12 years: 0-1.0 ng/mL<br>Follicular: 0.2-0.8 ng/mL<br>Luteal: 4.1-23.7 ng/mL<br>Mid-luteal: 4.5-25.2 ng/mL<br>Postmenopaus.: 0.1-0.6 ng/mL<br>1st trimester: 11.2-90.0 ng/mL<br>2nd trimester: 25.6-89.4 ng/mL<br>3rd trim: 48.4-422.5 ng/mL |

What is claimed:

1. A method for screening a patient's body fluid for a presence of angioinhibition resistance and treating the patient when angioinhibition resistance is identified, comprising the steps of:
   collecting a first blood or serum sample from the patient before administering an anti-antiogenic agent;
   administering to the patient the anti-angiogenic agent;
   collecting a second blood or serum sample from the patient after administration of the anti-angiogenic agent to the patient;

performing, on the first blood or serum sample and the second blood or serum sample, a chich chorioallantoic membrane (CAM) model estimate of angiogenesis stimulation, with the CAM configured for using the first collected blood or serum sample and the second blood or serum sample from the patient to quantify a generation of new blood vessels from existing blood vessels and new blood vessel branches;

determining from the CAM using the patient's second blood or serum sample as a function of comparing the generation of new blood vessels and branches before and after administering the anti-angiogenic agent an estimate of the patient's angioinhibition resistance;

and treating the patient when the estimate of the patient's angioinhibition resistance shows that the patient has angioinhibition resistance, wherein the step of treating the patient comprises inducing a state of subclinical hypothyroidism in the patient.

2. The method of claim 1 further comprising the step of identifying vascular branch points in the CAM angiogenesis assay, statistically comparing the CAM angiogenesis vascular branch points with blood or serum from a healthy patient and the second blood or serum sample collected after treatment with the anti-angiogenic agent.

3. The method of claim 1, wherein the anti-angiogenic agent is an anti-angiogenic thyroid hormone analog.

4. The method of claim 3, wherein the anti-angiogenic thyroid hormone analog is tetraiodothyroacetic acid (tetrac), triiodothyroacetic acid (triac), or a combination thereof.

5. The method of claim 4, wherein the anti-angiogenic thyroid hormone analog is further conjugated to a polymer, wherein the polymer is a nanoparticle.

6. The method of claim 5, wherein the polymer is selected from the group consisting of polyvinyl alcohol, acrylic acid ethylene co-polymer, polyethylene glycol (PEG), methoxy-polyethylene glycol-poly(lactide-co-glycolide), polyacrylic acid, polylactic acid, agarose, polyglycolide, polyethylene oxide, m-PEG, polyvinyl alcohol, polyglycolic acid, poly-L-lysine, Human Serum Albumin, carboxymethylcellulose derivatives, carboethylcellulose derivatives, carboxyhydroxypropylcellulose derivatives, hyaluronic acid, folate linked cyclodextrin, folate linked dextran, alginate, carrageenan, chitosan, dextran, collagen, polyamine, poly aniline, poly alanine, polytrytophan, poly tyrosine, polylactide-co-glycolide, poly(lactic-co-glycolic) acid (PLGA), polylysyl glycolide, polyglycolide, polylactide, or co-polymers thereof.

7. The method of claim 1, wherein the step of treating the patient further comprises administering a compound to the patient after inducing the state of subclinical hypothyroidism, wherein the compound is an anti-angiogenic agent, and anti-angiogenic agent encapsulating a chemotherapeutic agent, an anti-angiogenic agent encapsulating an anti-inflammatory agent, or a combination of compounds thereof.

8. The method of claim 1, wherein the step of inducing the state of subclinical hypothyroidism, includes the step of raising thyroid stimulating hormone (TSH) to approximately greater than 3.04 µIU/mL, by administering to the patient an anti-thyroid agent, decreasing the patient's production of the pro-angiogenic non-peptide hormone.

9. The method of claim 8, wherein the pro-angiogenic non-peptide hormone is a concentration of free $T_4$ or $T_3$.

* * * * *

UNITED STATES PATENT AND TRADEMARK OFFICE
CERTIFICATE OF CORRECTION

PATENT NO. : 10,060,934 B2
APPLICATION NO. : 14/546440
DATED : August 28, 2018
INVENTOR(S) : Shaker A. Mousa et al.

Page 1 of 1

It is certified that error appears in the above-identified patent and that said Letters Patent is hereby corrected as shown below:

In the Specification

Column 23, Line 2, delete "chich" and insert --chick--

In the Claims

Column 24, Line 19, delete "and" and insert --an--

Signed and Sealed this
Eleventh Day of December, 2018

Andrei Iancu
*Director of the United States Patent and Trademark Office*